(12) United States Patent
Baceiredo et al.

(10) Patent No.: US 10,442,825 B2
(45) Date of Patent: Oct. 15, 2019

(54) METHOD OF HYDROSILYLATION IMPLEMENTING AN ORGANIC CATALYST DERIVED FROM GERMYLENE

(71) Applicants: BLUESTAR SILICONES FRANCE SAS, Lyons (FR); CENTRE NATIONAL DE LA RECHERCHE SCIENTIFIQUE, Paris (FR)

(72) Inventors: Antoine Baceiredo, Toulouse (FR); Tsuyoshi Kato, Toulouse (FR); Yanli Mao, Toulouse (FR); Juliette Berthe, Paris (FR); Magali Bousquié, Lyons (FR)

(73) Assignees: Elkem Silicones France SAS, Lyons (FR); Centre National de la Recherche Scientifique, Paris (FR)

( * ) Notice: Subject to any disclaimer, the term of this patent is extended or adjusted under 35 U.S.C. 154(b) by 0 days.

(21) Appl. No.: 15/523,727

(22) PCT Filed: Nov. 12, 2015

(86) PCT No.: PCT/FR2015/053060
§ 371 (c)(1),
(2) Date: May 2, 2017

(87) PCT Pub. No.: WO2016/075414
PCT Pub. Date: May 19, 2016

(65) Prior Publication Data
US 2017/0313729 A1  Nov. 2, 2017

(30) Foreign Application Priority Data
Nov. 14, 2014 (FR) ..................... 14 61032

(51) Int. Cl.
*C07F 7/30* (2006.01)
*C07F 7/08* (2006.01)
*B01J 31/16* (2006.01)
*B01J 31/18* (2006.01)
*B01J 31/22* (2006.01)

(52) U.S. Cl.
CPC ............ *C07F 7/30* (2013.01); *B01J 31/1608* (2013.01); *B01J 31/187* (2013.01); *B01J 31/189* (2013.01); *B01J 31/2226* (2013.01); *C07F 7/0829* (2013.01); *B01J 2231/323* (2013.01); *B01J 2531/40* (2013.01)

(58) Field of Classification Search
None
See application file for complete search history.

(56) References Cited

PUBLICATIONS

Neumann, W. Chem Rev. 1991, 91, 311-334.*
Ferro et al. Inorg. Chem. 2012, 51, 1544-1551.*
Berthe, et al., "Synthesis and Reactivity of a Phosphine-Stabilized Monogermanium Analogue of Alkynes," J. Am. Chem. Soc'y, (2011) vol. 133: 15930-15933.
Garcia, et al., "Synthesis and Characterization of Rhodium Complexes with Phosphine-Stabilized Germylenes," Inorganic Chem., (2012) vol. 51: 8187-8193.
Takagi, et al., "Theoretical Study of Reactivity of Ge(II)-hydride Compound: Comparison with Rh(I)-Hydride Complex and Prediction of Full Catalytic Cycle by Ge(II)-hydride," J. Am. Chem. Soc'y, (2013) vol. 135: 8955-8965.
Hadlington, et al., "Low Coordinate Germanium(II) and Tin(II) Hydride Complexes: Efficient Catalysts for the Hydroboration of Carbonyl Compounds," J. Am. Chem. Soc'y, (2014) vol. 136: 3028-3031.

* cited by examiner

*Primary Examiner* — Clinton A Brooks
(74) *Attorney, Agent, or Firm* — McBee Moore Woodward & Vanik IP, LLC

(57) ABSTRACT

The present invention concerns a method for the hydrosilylation of an unsaturated compound comprising at least one ketone function, one aldehyde function, one alkene function and/or one alkyne function, with a compound comprising at least one hydrogen-silyl function implementing an organic catalyst of tri-coordinated germanium.

16 Claims, No Drawings

METHOD OF HYDROSILYLATION IMPLEMENTING AN ORGANIC CATALYST DERIVED FROM GERMYLENE

CROSS-REFERENCE TO RELATED APPLICATIONS

This application is a National Stage entry of International Application No. PCT/FR2015/053060, filed Nov. 12, 2015, which claims priority to French Patent Application No. 14 61032, filed Nov. 14, 2014.

BACKGROUND

Field of the Invention

The present invention relates to a process for the hydrosilylation of an unsaturated compound with a compound comprising at least one hydrogenosilyl function, catalyzed with tri-coordinate organogermanium compounds. The invention also relates to said tri-coordinate organogermanium compounds.

Description of Related Art

During a hydrosilylation reaction (also known as polyaddition), an unsaturated compound, i.e. a compound comprising at least one unsaturation of double or triple bond type, reacts with a compound comprising at least one hydrogenosilyl function, i.e. a hydrogen atom bonded to a silicon atom. This reaction may be described, for example, in the case of an unsaturation of C=O type such as that borne by ketone or aldehyde compounds, by:

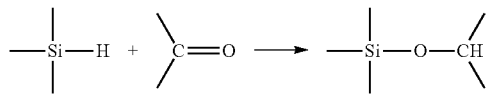

or, in the case of an unsaturation of alkene type, by:

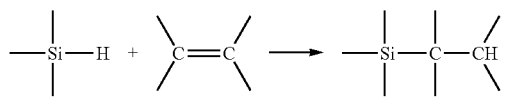

or alternatively, in the case of an unsaturation of alkyne type, by:

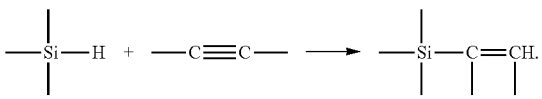

The hydrosilylation reaction of unsaturated compounds is performed by catalysis, using an organometallic catalyst. Currently, the organometallic catalyst that is suitable for this reaction is a platinum catalyst. Thus, the majority of the industrial hydrosilylation processes, in particular of alkenes, are catalyzed by the platinum Karstedt complex, of general formula $Pt_2(divinyltetramethyldisiloxane)_3$ (abbreviated as $Pt_2(DVTMS)_3$):

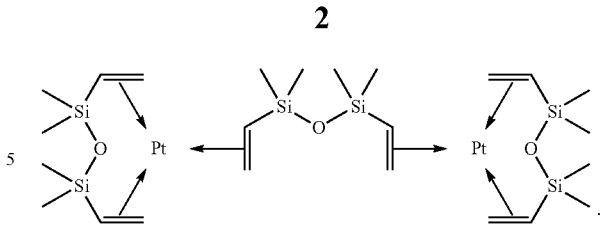

At the start of the 2000s, the preparation of platinum-carbene complexes of general formula:

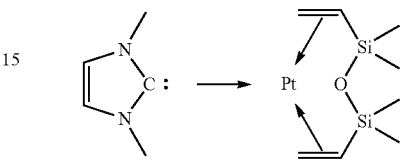

afforded access to more stable catalysts (see, for example, international patent application WO 01/42258).

However, the use of platinum organometallic catalysts is still problematic. It is a toxic, expensive metal that is becoming harder to find, and the price of which fluctuates enormously. It is therefore difficult to use at the industrial scale. It is thus desired to minimize the amount of catalyst required for the reaction, without, however, reducing the yield or the reaction rate. Moreover, it is desired to have available a catalyst that is stable over the course of the reaction. It has been found that, during the catalyzed reaction, platinum metal can precipitate, leading to the formation of insoluble colloids in the reaction medium. The catalyst is then less active. Furthermore, these colloids form cloudiness in the reaction medium, and the products obtained are not esthetically satisfying because they are colored.

In an increasingly competitive worldwide context in which the environment takes an increasingly important place each day, developing hydrosilylation processes catalyzed with more ecological and economical compounds is greatly desired. Metal-free organic catalysis is considered a promising approach for implementing these green chemistry concepts.

However, organic catalysts are unstable in air and degrade rapidly, which makes them particularly difficult to use. This is the case, for example, for germanium hydride organic compounds, which are known to degrade rapidly in air (*Angew. Chem. Int.* Ed. 2006, 45, 2602-2605).

In addition, the reactivity of these organic catalysts is often poorer than that of organometallic derivatives.

Thus, one of the objects of the present invention is to propose a hydrosilylation process catalyzed with a novel type of organic compound which is stable in air and in the reaction medium, and which has good reactivity.

The inventors of the present patent application have developed a hydrosilylation process catalyzed with tri-coordinate organogermanium compounds. They have demonstrated, entirely surprisingly, that the particular cyclic structure of these compounds, bearing an alkoxy group bonded to the germanium atom, and a phosphine group, makes it possible for the first time to obtain tri-coordinate organogermanium compounds which are stable in air and in the reaction medium, which have good reactivity with respect to the hydrosilylation reaction and, consequently, which can catalyze said hydrosilylation process.

The reactivity of a tri-coordinate germanium hydride, ($^{Dip}$NacNac)GeH, formed the subject of a theoretical projection by Takagi et al. (*J. Am. Chem. Soc.*, 2013, 135, 8955-8965) by the density functional theory (DFT calculation). The calculations appear to indicate that, theoretically, tri-coordinate germanium hydride might be a catalyst for a ketone hydrosilylation reaction. However, the subsequent experiments performed by Hadlington et al. (*J. Am. Chem. Soc.*, 2014, 136, 3028-3031) revealed that the tri-coordinate germanium hydride ($^{Dip}$NacNac)GeH reacts only with activated ketones, and that its reactivity is less than that of compounds of bi-coordinate germanium hydride type. Hadlington et al. explains that the bi-coordinate compound is more reactive since it is less stable than the tri-coordinate compound. Thus, Hadlington et al. suggests that increasing the stability of the germanium hydrides would bring about a reduction in their reactivity.

The inventors of the present patent application have, however, demonstrated that certain tri-coordinate organogermanium compounds of specific formula, which are structurally stabilized, can efficiently catalyze hydrosilylation processes.

SUMMARY

One subject of the present invention is a process for the hydrosilylation of an unsaturated compound (A) comprising at least one ketone function, aldehyde function, alkene function and/or alkyne function, with a compound (B) comprising at least one hydrogenosilyl function, said process being characterized in that it is catalyzed with an organic compound (C) represented by Formula 1:

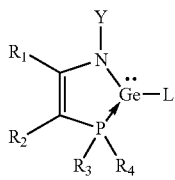

Formula 1 in which

L is an alkoxy group comprising from 1 to 18 carbon atoms,

Y is an alkyl group containing from 1 to 20 carbon atoms or an aryl group containing from 6 to 18 carbon atoms, the groups $R_1$ and $R_2$, which may be identical or different, represent a hydrogen atom, an alkyl group containing from 1 to 20 carbon atoms, an alkenyl group containing from 2 to 12 carbon atoms, an aryl group containing from 6 to 18 carbon atoms, $R_1$ and $R_2$ together possibly forming a saturated or unsaturated, substituted ring of 5 to 8 atoms, and in the phosphine group

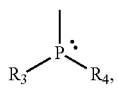

the groups $R_3$ and $R_4$, which may be identical or different, represent a hydrogen atom, a halogen atom, an alkyl or a haloalkyl group containing from 1 to 20 carbon atoms, a cycloalkyl group containing from 3 to 20 carbon atoms, a cycloalkyl-alkyl group containing from 4 to 40 carbon atoms, an aryl group containing from 6 to 18 carbon atoms, an aryl-alkyl group containing from 6 to 38 carbon atoms; $R_3$ and $R_4$ also possibly forming, with the atoms to which they are attached, a monocyclic or polycyclic ring consisting of 3 to 20 atoms.

Finally, a subject of the invention is also an organic compound (C) represented by Formula 1:

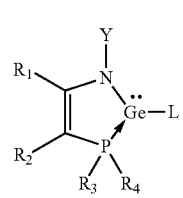

Formula 1 in which

L is an alkoxy group comprising from 1 to 18 carbon atoms,

Y is an alkyl group containing from 1 to 20 carbon atoms or an aryl group containing from 6 to 18 carbon atoms, the groups $R_1$ and $R_2$, which may be identical or different, represent a hydrogen atom, an alkyl group containing from 1 to 20 carbon atoms, an alkenyl group containing from 2 to 12 carbon atoms, an aryl group containing from 6 to 18 carbon atoms, $R_1$ and $R_2$ together possibly forming a saturated or unsaturated, substituted ring of 5 to 8 atoms, and in the phosphine group

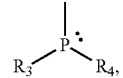

the groups $R_3$ and $R_4$, which may be identical or different, represent a hydrogen atom, a halogen atom, an alkyl or a haloalkyl group containing from 1 to 20 carbon atoms, a cycloalkyl group containing from 3 to 20 carbon atoms, a cycloalkyl-alkyl group containing from 4 to 40 carbon atoms, an aryl group containing from 6 to 18 carbon atoms, an aryl-alkyl group containing from 6 to 38 carbon atoms; $R_3$ and $R_4$ also possibly forming, with the atoms to which they are attached, a monocyclic or polycyclic ring consisting of 3 to 20 atoms.

These organic compounds are particularly suitable for use as hydrosilylation catalyst, which also constitutes a subject of the present invention.

Finally, a subject of the invention is a composition comprising:
- at least one unsaturated compound (A) comprising at least one ketone function, aldehyde function, alkene function and/or alkyne function,
- at least one compound (B) comprising at least one hydrogenosilyl function, and
- a catalyst chosen from the organic compounds (C) of Formula 1 as defined above.

DETAILED DESCRIPTION OF A PREFERRED EMBODIMENT

Process

According to a first aspect, the present invention relates to a process for the hydrosilylation of an unsaturated compound (A), i.e. a compound comprising at least one unsaturation of double or triple bond type, said unsaturation being borne by at least one ketone function, aldehyde function, alkene function and/or alkyne function, preferably borne by at least one alkene function and/or at least one alkyne function, with a compound (B) comprising at least one hydrogenosilyl function (≡Si—H), said process being characterized in that it is catalyzed with an organic compound (C) represented by Formula 1:

Formula 1

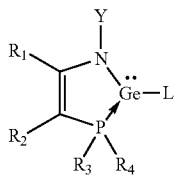

in which

L is an alkoxy group comprising from 1 to 18 carbon atoms,

Y is an alkyl group containing from 1 to 20 carbon atoms or an aryl group containing from 6 to 18 carbon atoms, the groups $R_1$ and $R_2$, which may be identical or different, represent a hydrogen atom, an alkyl group containing from 1 to 20 carbon atoms, an alkenyl group containing from 2 to 12 carbon atoms, an aryl group containing from 6 to 18 carbon atoms, $R_1$ and $R_2$ together possibly forming a saturated or unsaturated, substituted ring of 5 to 8 atoms, and in the phosphine group

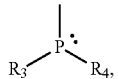

the groups $R_3$ and $R_4$, which may be identical or different, represent a hydrogen atom, a halogen atom, an alkyl or a haloalkyl group containing from 1 to 20 carbon atoms, a cycloalkyl group containing from 3 to 20 carbon atoms, a cycloalkyl-alkyl group containing from 4 to 40 carbon atoms, an aryl group containing from 6 to 18 carbon atoms, an aryl-alkyl group containing from 6 to 38 carbon atoms; $R_3$ and $R_4$ also possibly forming, with the atoms to which they are attached, a monocyclic or polycyclic ring consisting of 3 to 20 atoms.

The organic compound (C) is characterized in that it comprises a cyclic structure around the tri-coordinate germanium atom, an alkoxy group bonded to the germanium atom, and a phosphine group which donates an electron pair to the germanium atom.

The Applicant has demonstrated that this particular cyclic structure makes it possible to stabilize the organic compound (C) without, however, impairing its reactivity.

According to the invention, the term "tri-coordinate germanium" means a germanium atom covalently bonded to at least two substituents, and to a third via dative bonding. In the case of the organic compound (C), the germanium atom is bonded to a nitrogen atom and to a ligand L via covalent bonds, and to the phosphine group via a dative bond generated by the phosphorus atom.

According to the invention, the term "alkyl" means a linear or branched saturated hydrocarbon-based chain containing from 1 to 20 carbon atoms and preferably from 1 to 8 carbon atoms. An alkyl group may be chosen from methyl, ethyl, isopropyl, n-propyl, tert-butyl, isobutyl, n-butyl, n-pentyl, isoamyl and 1,1-dimethylpropyl groups.

According to the invention, the term "alkoxy" means an alkyl group as defined above bonded to an oxygen atom, preferably containing from 1 to 18 carbon atoms, more preferentially from 1 to 6 carbon atoms. An alkoxy group may be chosen from methoxy, ethoxy, propoxy and butoxy groups.

According to the invention, the term "halogen atom" means an atom chosen from the group formed by fluorine, chlorine, bromine and iodine.

According to the invention, the term "alkenyl" means a linear or branched unsaturated hydrocarbon-based chain containing from 2 to 12 carbon atoms.

According to the invention, the term "haloalkyl" means an alkyl group as defined above substituted with a halogen atom as defined above.

According to the invention, the term "cycloalkyl" means a saturated monocyclic or polycyclic, preferably monocyclic or bicyclic, hydrocarbon-based group containing from 3 to 20 carbon atoms, preferably from 3 to 8 carbon atoms. When the cycloalkyl group is polycyclic, the multiple cyclic nuclei may be attached to each other via a covalent bond and/or via a spirane atom and/or may be fused with each other. A cycloalkyl group may be chosen from cyclopropyl, cyclobutyl, cyclopentyl, cyclohexyl, cycloheptyl, cyclooctyl, adamantane and norbornane groups.

According to the invention, the term "cycloalkyl-alkyl" means a cycloalkyl group as defined above substituted with an alkyl group also as defined above.

According to the invention, the term "aryl" means a monocyclic or polycyclic aromatic hydrocarbon-based group containing from 6 to 18 carbon atoms. An aryl group may be chosen from phenyl, naphthyl, anthracenyl and phenanthryl groups.

According to the invention, the term "aryl-alkyl" means an aryl group as defined above substituted with an alkyl group also as defined above.

The term "acyl" means an alkyl, cycloalkyl or aryl group as defined above bonded to a C=O group.

According to the invention, the term "amine" means a primary amine group or a secondary, tertiary or quaternary amine group whose substituent(s) are chosen from an alkyl group as defined above.

According to a particularly preferred embodiment of the invention, the ligand L of the organic compound (C) is the ethoxy group.

Advantageously, the ligand L makes it possible to stabilize the organic compound (C) without impairing its reactivity when it catalyzes the process according to the invention.

According to one embodiment of the invention, the groups $R_3$ and $R_4$ borne by the phosphine group can form a ring formed from 3 to 20 atoms, optionally comprising one or more unsaturations, and optionally comprising one or more heteroatoms chosen from O, N, Si and P. The monocyclic or polycyclic ring may optionally be substituted one or more times with a halogen atom, with an alkyl group, with a cycloalkyl group, with a cycloalkyl-alkyl group, with an aryl group, with an aryl-alkyl group, with an acyl group, with an amine group, with a hydroxyl group or with an alkoxy group.

According to a preferred embodiment, $R_3$ and $R_4$ form, with the atoms to which they are attached, a monocycle formed from 3 to 10 atoms, preferably from 3 to 6 atoms. Preferably, said monocycle is saturated and may optionally comprise one or more heteroatoms chosen from N, Si and P, preferably from N and Si. Said monocycle may also be substituted one or more times with an alkyl group and/or with an aryl-alkyl group, even more preferentially with an alkyl group.

According to a particularly preferred embodiment, the phosphine group borne by the organic compound (C) is represented by the formulae:

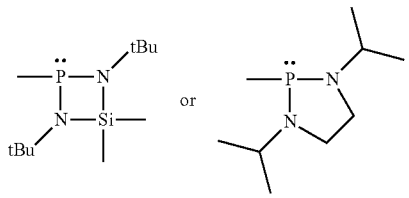

in which tBu is the tert-butyl group.

Without wishing to be bound by any theory, the phosphine group appears to allow intramolecular complexation of the germanium atom in the organic compound (C), thus improving its stability in air and in the reaction medium.

In the organic compound (C), the group Y is an alkyl group containing from 1 to 20 carbon atoms or an aryl group containing from 6 to 18 carbon atoms. Preferably, the group Y is a $C_6$-$C_{10}$ aryl group substituted one or more times with an alkyl group and/or with an aryl-alkyl group. More preferentially, the group Y is a phenyl group substituted with an alkyl group, in particular with methyl and/or isopropyl.

According to a particularly preferred embodiment of the invention, the group Y is chosen from 2,6-iPr$_2$—C$_6$H$_3$ and 2,4,6-trimethyl-C$_6$H$_2$.

Advantageously, the group Y makes it possible to stabilize said compound without impairing its reactivity when it catalyzes the process according to the invention.

In the organic compound (C) represented by Formula 1, the groups $R_1$ and $R_2$, which may be identical or different, represent a hydrogen atom, an alkyl group containing from 1 to 20 carbon atoms, an alkenyl group containing from 2 to 12 carbon atoms, an aryl group containing from 6 to 18 carbon atoms, $R_1$ and $R_2$ together possibly forming a saturated or unsaturated, substituted ring of 5 to 8 atoms.

Preferably, $R_1$ and $R_2$ may together form a substituted ring of 6 atoms in which two substituents form a 1-atom bridge on said ring.

According to a preferred embodiment of the invention, the organic compound (C) has the following structure:

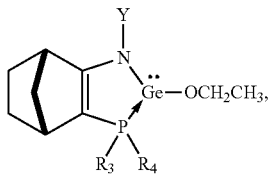

in which
Y is 2,6-iPr$_2$—C$_6$H$_3$ or 2,4,6-trimethyl-C$_6$H$_2$, and
the phosphine group is represented by the formulae:

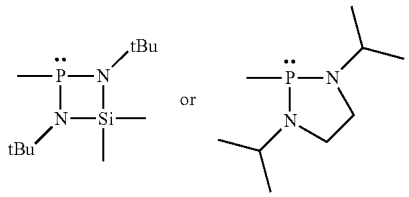

in which tBu is the tert-butyl group.

According to another more preferred embodiment of the invention, the organic compound (C) has the following structure:

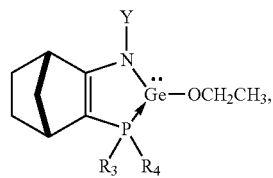

in which
Y is 2,4,6-trimethyl-C$_6$H$_2$,
the phosphine group is represented by the formula:

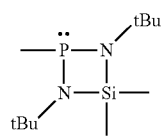

in which tBu is the tert-butyl group.

The unsaturated compound (A) used in the hydrosilylation process according to the invention is a chemical compound comprising at least one unsaturation not forming part of an aromatic ring. The unsaturated compound (A) comprises at least one ketone function, aldehyde function, alkene function and/or alkyne function. Any compound comprising at least one ketone, aldehyde, alkene and/or alkyne function may be used in the process according to the invention, insofar as it does not contain a reactive chemical function that might hamper or even prevent the hydrosilylation reaction.

According to one embodiment, the unsaturated compound (A) comprises one or more ketone functions and from 2 to 40 carbon atoms. The unsaturated compound (A) may then preferably be chosen from trifluoroacetophenone, diethyl ketone and acetophenone.

According to another embodiment, the unsaturated compound (A) comprises one or more aldehyde functions and from 2 to 40 carbon atoms. The unsaturated compound (A) may then preferably be chosen from hexanal, 4-fluorobenzaldehyde and benzaldehyde.

According to a particularly preferred embodiment, the unsaturated compound (A) used in the hydrosilylation process according to the invention comprises at least one alkene function and/or alkyne function.

According to another preferred embodiment, the unsaturated compound (A) comprises one or more alkene functions and from 2 to 40 carbon atoms. According to another preferred embodiment, the unsaturated compound (A) comprises one or more alkyne functions and from 2 to 40 carbon atoms.

The unsaturated compound (A) may preferably be chosen from the group formed by acetylene, $C_1$ to $C_4$ alkyl acrylates and methacrylates, acrylic or methacrylic acid, alkenes, preferably octene and more preferentially 1-octene, allyl alcohol, allylamine, allyl glycidyl ether, allyl piperidyl ether, preferentially sterically hindered allyl piperidyl ether, styrenes, preferentially alpha-methylstyrene, 1,2-epoxy-4-vinylcyclohexane, allyl chloride, chloroalkenes, preferably allyl chloride and fluoroalkenes, preferably 4,4,5,5,6,6,7,7,7-nonafluoro-1-heptene.

The unsaturated compound (A) may be chosen from compounds comprising several alkene functions, preferably two or three alkene functions, and, particularly preferably, compound (A) is chosen from the following compounds:

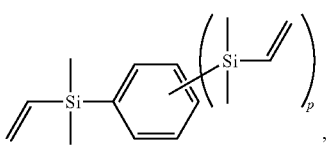

with p being 1 or 2,

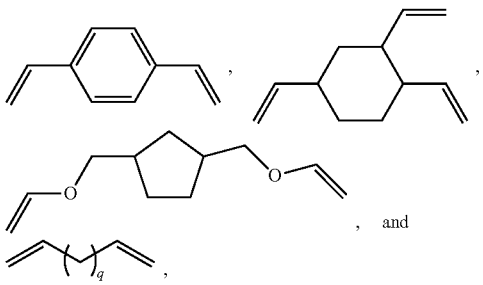

, and with q being from 2 to 6, preferably q being 2 or 4.

The unsaturated compound (A) may also be chosen from organopolysiloxane compounds (commonly referred to as POS) comprising units of formula (I):

$$A_g U_h SiO_{(4-(g+h))/2} \qquad (I)$$

in which:
the radicals A, which may be identical or different, represent a linear or branched alkenyl or alkynyl radical containing between 2 and 6 carbon atoms;
the radicals U, which may be identical or different, represent a monovalent radical other than a hydrogen atom,
g and h represent integers, g being 1 or 2, h being 0, 1 or 2 and (g+h) being 1, 2 or 3; and optionally comprising other units of formula (II):

$$U_i SiO_{(4-i)/2} \qquad (II)$$

in which U has the same meaning as above, and i represents an integer from 0 to 3.

In formula (I) and in formula (II), U may represent a monovalent radical chosen from the group formed by an alkyl group containing 1 to 8 carbon atoms, optionally substituted with at least one halogen atom, and an aryl group. U may advantageously represent a monovalent radical chosen from the group formed by methyl, ethyl, propyl, 3,3,3-trifluoropropyl, xylyl, tolyl and phenyl.

Examples of organopolysiloxanes that may be unsaturated compounds (A) according to the invention are:
a poly(dimethylsiloxane) bearing dimethylvinylsilyl end groups;
a poly(dimethylsiloxane-co-methylphenylsiloxane) bearing dimethylvinylsilyl end groups;
a poly(dimethylsiloxane-co-methylvinylsiloxane) bearing dimethylvinylsilyl end groups; and
a poly(dimethylsiloxane-co-methylvinylsiloxane) bearing trimethylsilyl end groups; and
a cyclic poly(methylvinylsiloxane).

The hydrosilylation process according to the invention also uses a compound (B) comprising at least one hydrogenosilyl function. According to one embodiment, compound (B) comprising at least one hydrogenosilyl function is a silane or polysilane compound comprising at least one hydrogen atom bonded to a silicon atom.

In the present invention, the term "silane" compound means chemical compounds comprising a silicon atom bonded to four hydrogen atoms or to organic substituents. In the present invention, the term "polysilane" compound means chemical compounds bearing at least one ≡Si—Si≡ unit.

According to a particularly preferred embodiment, compound (B) is phenylsilane.

Compound (B) may also be an organopolysiloxane compound comprising at least one hydrogen atom bonded to a silicon atom. In the present invention, the term "organopolysiloxane" compound means chemical compounds bearing at least one ≡Si—O—Si≡ unit. The organopolysiloxane compound comprises at least two silicon atoms, preferably at least three or more silicon atoms. Said organopolysiloxane compound may advantageously be an organopolysiloxane (commonly referred to as POS) comprising at least one unit of formula (III):

$$H_d U_e SiO_{(4-(d+e))/2} \qquad (III)$$

in which:
the radicals U, which may be identical or different, represent a monovalent radical other than a hydrogen atom,
d and e represent integers, d being 1 or 2, e being 0, 1 or 2 and (d+e) being 1, 2 or 3; and optionally other units of formula (IV):

$$U_f SiO_{(4-f)/2} \qquad (IV)$$

in which U has the same meaning as above, and f represents an integer between 0 and 3.

It is understood in formula (III) and in formula (IV) above that, if several groups U are present, they may be identical to or different from each other.

In formula (III), the symbol d may preferentially be equal to 1.

Furthermore, in formula (III) and in formula (IV), U may represent a monovalent radical chosen from the group formed by an alkyl group containing 1 to 8 carbon atoms, optionally substituted with at least one halogen atom, and an aryl group. U may advantageously represent a monovalent radical chosen from the group formed by methyl, ethyl, propyl, 3,3,3-trifluoropropyl, xylyl, tolyl and phenyl. Examples of units of formula (III) are the following: $H(CH_3)_2SiO_{1/2}$, $HCH_3SiO_{2/2}$ and $H(C_6H_5)SiO_{2/2}$.

The organopolysiloxane may have a linear, branched, cyclic or network structure. Examples of organopolysiloxanes that may be organopolysiloxane compounds comprising at least one hydrogen atom bonded to a silicon atom are:
a poly(dimethylsiloxane) bearing hydrogenodimethylsilyl end groups;
a poly(dimethylsiloxane-co-methylhydrogenosiloxane) bearing trimethylsilyl end groups;
a poly(dimethylsiloxane-co-methylhydrogenosiloxane) bearing hydrogenodimethylsilyl end groups;
a poly(methylhydrogenosiloxane) bearing trimethylsilyl end groups; and
a cyclic poly(methylhydrogenosiloxane).

Preferably, compound (B) is an organopolysiloxane compound comprising, per molecule, at least two hydrogenosilyl functions (Si—H).

Finally, compound (B) may be an organic polymer comprising hydrogenosilyl functions in end positions. The organic polymer may be, for example, a polyoxyalkylene, a saturated hydrocarbon-based polymer or a poly(meth)acrylate. Organic polymers comprising reactive functions in end positions are described especially in patent applications US 2009/0182099 and US 2009/0182091.

According to a particular embodiment of the present invention, it is possible for the unsaturated compound (A) and compound (B) comprising at least one hydrogenosilyl function to be the same compound, on the one hand comprising at least one ketone function, aldehyde function, alkene function and/or alkyne function, and on the other hand comprising at least one silicon atom and at least one hydrogen atom bonded to the silicon atom. This compound may then be termed "difunctional", and it is capable of reacting with itself via a hydrosilylation reaction. The invention may thus also relate to a process for the hydrosilylation of a difunctional compound with itself, said difunctional compound on the one hand comprising at least one ketone function, aldehyde function, alkene function and/or alkyne function—preferably at least one alkene function and/or at least one alkyne function—, and on the other hand comprising at least one silicon atom and at least one hydrogen atom bonded to the silicon atom, said process being characterized in that it is catalyzed with an organic compound (C) as described above.

Examples of organopolysiloxanes that may be difunctional compounds are:
- a poly(dimethylsiloxane-co-hydrogenomethylsiloxane-co-vinylmethylsiloxane) bearing dimethylvinylsilyl end groups;
- a poly(dimethylsiloxane-co-hydrogenomethylsiloxane-co-vinylmethylsiloxane) bearing dimethylhydrogenosilyl end groups; and
- a poly(dimethylsiloxane-co-hydrogenomethylsiloxane-co-propyl glycidyl ether-methylsiloxane) bearing trimethylsilyl end groups.

When it is a matter of using the unsaturated compound (A) and compound (B) comprising at least one hydrogenosilyl function, a person skilled in the art understands that this also means the use of a difunctional compound.

The hydrosilylation reaction may be performed in a solvent or in the absence of solvent. As a variant, one of the reagents, for example the unsaturated compound (A), may act as solvent. Suitable solvents are solvents that are miscible with compound (B).

The hydrosilylation reaction may be performed at a temperature of between 15° C. and 300° C., preferentially between 20° C. and 240° C., more preferentially between 70° C. and 200° C., more preferentially between 50° C. and 140° C., and even more preferentially between 50° C. and 100° C.

Organic Compound (C)

A subject of the invention is also an organic compound (C) represented by Formula 1 described previously, including all the embodiments of said organic compound described previously.

Use

A subject of the present invention is also the use of an organic compound (C) described previously as a hydrosilylation catalyst.

Composition

A subject of the present invention is also a composition comprising:
- at least one unsaturated compound (A) comprising at least one ketone function, aldehyde function, alkene function and/or alkyne function,
- at least one compound (B) comprising at least one hydrogenosilyl function, and
- a catalyst chosen from the organic compounds (C) represented by Formula 1.

This composition forms the reaction medium in which the hydrosilylation reaction according to the invention may take place. To do this, this composition may be heated as described above.

The relative amount of compound (A) and of compound (B) may be controlled so as to ensure a rate of reaction of the unsaturations with hydrogenosilyl functions. The mole ratio of the Si—H functions of compounds (B) to the alkene and alkyne functions of compounds (A) is between 1:100 and 100:1, preferably between 1:10 and 10:1 and more preferably between 1:5 and 5:1. According to one embodiment, the mole ratio of the Si—H functions of compounds (B) to the alkene and alkyne functions of compounds (A) is strictly less than 1. The Si—H functions are, here, in deficit relative to the unsaturated functions. According to another embodiment, the mole ratio of the Si—H functions of compounds (B) to the alkene and alkyne functions of compounds (A) is strictly greater than 1. The Si—H functions are then in excess relative to the unsaturated functions.

According to the invention, the molar concentration of catalyst in the composition is from 0.5% to 10%, preferably from 1% to 7.5% and more preferably from 1.5% to 5.5% relative to the number of moles of unsaturated compound (A).

Specifically, during the hydrosilylation reaction, the unsaturated compound (A) is usually in deficit, and the molar concentration of catalyst is expressed relative to the number of moles of compound (A) in deficit. In the hypothesis in which, during the hydrosilylation reaction, compound (B) comprising at least one hydrogenosilyl function is in deficit, the molar concentration of catalyst in the composition would be from 0.5% to 10%, preferably from 1% to 7.5% and more preferably from 1.5% to 5.5% relative to the number of moles of compound (B) in deficit. Besides the unsaturated compound (A) and compound (B) comprising at least one hydrogenosilyl function, the composition of the invention may optionally comprise additives.

According to one embodiment of the invention, the additive may be an inhibitor or retarder for the hydrosilylation reaction. These compounds are known to those skilled in the art and are commercially available. Mention may be made, for example, of the following compounds: organopolysiloxanes substituted with at least one alkenyl which may optionally be in cyclic form, tetramethylvinyltetrasiloxane being particularly preferred; pyridine; organic phosphines and phosphites; unsaturated amides; alkyl maleates; and acetylenic alcohols.

The acetylenic alcohols (described, for example, in patents FR 1 528 464 and FR 2 372 874), which are among the preferred hydrosilylation reaction thermal blockers, have the formula:

(R')(R")C(OH)—C≡CH in which formula R' is a linear or branched alkyl radical, or a phenyl radical; R" is a hydrogen atom or a linear or branched alkyl radical, or a phenyl radical; the radicals R' and R" and the carbon atom alpha to the triple bond optionally being able to form a ring; the total number of carbon atoms contained in R' and R" being at least 5, preferably from 9 to 20.

For said acetylenic alcohols, examples that may be mentioned include:
- 1-ethynyl-1-cyclohexanol;
- 3-methyl-1-dodecyn-3-ol;
- 3,7,11-trimethyl-1-dodecyn-3-ol;
- 1,1-diphenyl-2-propyn-1-ol;
- 3-ethyl-6-ethyl-1-nonyn-3-ol;
- 2-methyl-3-butyn-2-ol;
- 3-methyl-1-pentadecyn-3-ol; and
- diallyl maleate or diallyl maleate derivatives.

The compositions of the invention may also comprise common functional additives. Families of common functional additives that may be mentioned include:
- fillers;
- adhesion promoters;
- adhesion modifiers;
- heat-resistant additives;
- consistency-enhancing additives;
- pigments; and
- heat-resistant, oil-resistant or fire-resistant additives, for example metal oxides.

The fillers optionally envisaged are preferably mineral. They may especially be siliceous. When they are siliceous materials, they may act as reinforcing or semi-reinforcing filler. The reinforcing siliceous fillers are chosen from colloidal silicas, powders of fumed silica and of precipitated silica, or mixtures thereof. These powders have a mean particle size generally less than 0.1 μm (micrometers) and a BET specific surface area of greater than 30 m$^2$/g, preferably between 30 and 350 m$^2$/g. Semi-reinforcing siliceous fillers such as diatomaceous earths or ground quartz may also be used. As regards the nonsiliceous mineral materials, they may be involved as a semi-reinforcing or bulking mineral filler. Examples of these nonsiliceous fillers that may be used, alone or as a mixture, are carbon black, titanium dioxide, aluminum oxide, hydrated alumina, expanded vermiculite, non-expanded vermiculite, calcium carbonate optionally surface-treated with fatty acids, zinc oxide, mica, talc, iron oxide, barium sulfate and slaked lime. These fillers have a particle size generally between 0.001 and 300 μm (micrometers) and a BET surface area of less than 100 m$^2$/g. In practical but nonlimiting terms, the fillers used may be a mixture of quartz and silica. The fillers may be treated with any suitable product. In terms of weight, use is preferably made of an amount of filler of between 1% and 50% by weight and preferably between 1% and 40% by weight relative to all the constituents of the composition.

More generally, in quantitative terms, the compositions according to the invention may have standard proportions in the technical field under consideration, given that the intended application must also be taken into account.

Other aims, characteristics and advantages of the invention will emerge from the examples that follow, which are given as purely nonlimiting illustrations.

EXAMPLES

All the experiments were performed under an argon atmosphere insofar as they use air-sensitive reagents such as Ge—Cl$_4$, n-BuLi or trichlorophosphine, using standard techniques in gloveboxes and Schlenk tubes. Oxygen-free dry solvents were used. The $^1$H, $^{13}$C, $^{29}$Si and $^{31}$P NMR spectra were recorded on Brüker Avance 300 MHz spectrometers. The chemical shifts of the $^1$H, $^{13}$C and $^{29}$Si NMR spectra are indicated in ppm relative to (CH$_3$)$_4$Si used as internal standard. The chemical decreases of the $^{31}$P NMR spectra are expressed in ppm relative to 85% H$_3$PO$_4$. The chemical shifts of the $^{119}$Sn NMR spectra and the correlations of the $^1$H BMR spectra were obtained using standard procedures.

Example 1: Synthesis of a Compound C1 of Formula 1

Compound C1 was synthesized, having the formula:

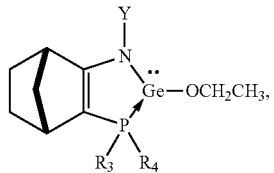

in which
Y is 2,6-iPr$_2$—C$_6$H$_3$, and
the phosphine group is represented by the formula:

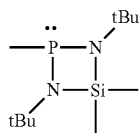

in which tBu is the tert-butyl group
from the following compounds:
Synthesis of the Germanium Dichloride—Dioxane Complex (Ge—Cl$_2$-dioxane)

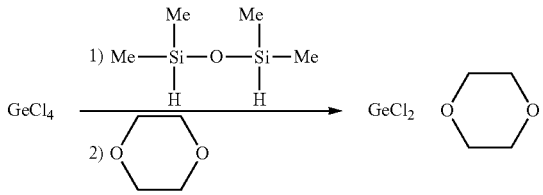

Tetrachlorogermane (11.4 mL, 98 mmol), diethyl ether (50 mL) and tetramethyldisiloxane (18.7 mL, 106 mmol) were placed in a two-necked Schlenk tube equipped with a condenser. The solution was heated gently at reflux until it became clear, followed by sudden phase separation. This reaction was continued for a further 2 hours to ensure that all the product was deposited. The colorless upper phase was transferred carefully into a conical flask and deactivated by adding ethanol dropwise. 1,4-Dioxane (13.7 mL, 160 mmol) was added dropwise to the remaining yellow phase. A white solid precipitated and was collected by filtration under an argon atmosphere, rinsing the solid with pentane. The white solid corresponding to Ge—Cl$_2$-dioxane was then dried and stored in a glovebox (16.8 g, 74%).

Synthesis of Compound 2

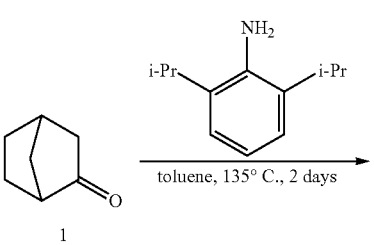

-continued

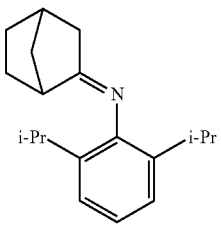

2

Norcamphor 1 (30 g, 0.3 mol), diisopropylaniline (57 ml, 0.3 mol), a catalytic amount of para-toluenesulfonic acid (0.58 g, 3 mmol) and toluene (150 ml) were placed in a 500 ml two-necked round-bottomed flask equipped with a condenser and Dean-Stark apparatus. The mixture was heated at reflux for 3 days at 135° C. (oil bath temperature). The solvent was evaporated off and the oil was taken up in pentane and filtered to remove a small amount of precipitate. The solution was left to evaporate slowly for crystallization at room temperature. A colorless crystal corresponding to compound 2 was collected 2 days later (60 g, 74%).

NMR Analysis of Compound 2

$^1$H NMR (300 MHz, C$_6$D$_6$, ppm) δ=1.09 (d, J$_{HH}$=6.8 Hz, 3H, CH$_{3i-Pr}$), 1.10 (d, J$_{HH}$=6.7 Hz, 3H, CH$_{3i-Pr}$), 1.12 (d, J$_{HH}$=6.3 Hz, 3H, CH$_{3i-Pr}$), 1.13 (d, J$_{HH}$=6.9 Hz, 3H, CH$_{3i-Pr}$), 1.21-1.89 (m, 8H, CH$_2$), 2.44 (m, 1H, CH$_{tdp}$), 2.75 (sept, J$_{HH}$=6.8 Hz, 1H, CH$_{i-Pr}$), 2.82 (sept, J$_{HH}$=6.8 Hz, 1H, CH$_{i-Pr}$), 2.98 (m, 1H, CH$_{tdp}$), 7.03 (m, 3H, CH$_{ar}$);

$^{13}$C{1H} (75 MHz, C$_6$D$_6$, ppm) δ=22.7 (s, CH$_{3i-Pr}$), 22.9 (s, CH$_{3i-Pr}$), 23.4 (s, CH$_{3i-Pr}$), 23.6 (s, CH$_{3i-Pr}$), 26.5 (s, CH$_2$), 27.6 (s, CH$_2$), 27.7 (s, CH$_{i-Pr}$), 28.0 (s, CH$_{i-Pr}$), 35.9 (s, CH$_{tdp}$), 38.2 (s, CH$_2$), 38.8 (s, CH$_2$), 47.0 (s, CH$_{tdp}$), 123.0 (s, CH$_{ar}$), 123.1 (s, CH$_{ar}$), 123.4 (s, CH$_{ar}$), 135.8 (s, C$_{ar}$), 136.2 (s, C$_{ar}$), 147.0 (s, C$_{ar}$), 179.9 (s, C=N).

Synthesis of Compound 5

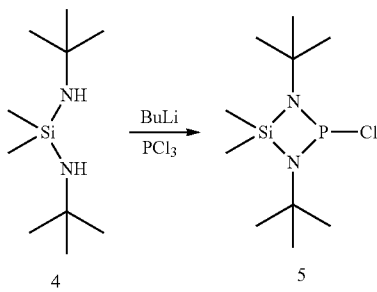

To a stirred solution of Me$_2$Si(NH$^t$Bu)$_2$ 4 (7.38 g, 36.46 mmol) in 40 ml of THF at −78° C. were added 46.7 mL (74.47 mmol) of a solution of n-BuLi in hexane (1.6 M). After the addition, the solution was heated at 50° C. for 4 hours. A solution of PCl$_3$ (3.2 mL, 36.58 mmol) was added dropwise at −100° C. to the above solution and the temperature was maintained below −100° C. for 2 hours. The solution was then heated slowly to room temperature overnight. The solvent was evaporated off under vacuum and the residue taken up in 40 mL of pentane. The mixture was filtered and the residue was extracted twice with 20 mL of pentane. The pentane was evaporated off under vacuum and the residue purified by distillation under vacuum to give compound 5 (7.0 g, 72%) in the form of a colorless oil.

NMR analysis of compound 5

$^1$H NMR (300 MHz, CDCl$_3$, ppm) δ=0.45 (s, 6H, SiCH$_3$), 1.23 (d, J$_{PH}$=1.3 Hz, 18H, CH$_{3t-Bu}$);

$^{13}$C NMR{1H} (75 MHz, CDCl$_3$, ppm) δ=5.2 (d, J$_{PC}$=3.6 Hz, SiCH$_3$), 31.9 (d, J$_{PC}$=7.8 Hz, CH$_{3t-Bu}$), 52.0 (d, J$_{PC}$=7.8 Hz, C$_{t-Bu}$);

$^{31}$P NMR {1H} (121 MHz, CDCl$_3$, ppm) δ=212.3;

$^{29}$Si NMR {1H} (59 MHz, CDCl$_3$, ppm) δ=27.2.

Synthesis of Compound 8

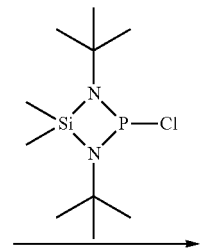

2

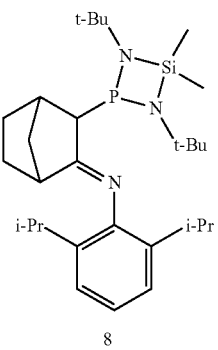

8

To a stirred solution of compound 2 prepared previously (10.0 g, 37.1 mmol) in 80 ml of THF at −78° C. was added nBuLi (1.6 M, 24.3 mL, 39 mmol) and this mixture was then left to warm to room temperature over 1 hour with stirring. The solution was again cooled to −78° C. and compound 5 prepared previously (9.9 g, 37.1 mmol) was added. The mixture was left to warm to room temperature and the solvent was evaporated off under vacuum. The solid was washed with acetonitrile (three times, 80 ml), dried and dissolved with pentane, and then filtered. The volatile substances were removed to obtain compound 8 (17.4 g, 94%) in the form of a white solid.

NMR Analysis of Compound 8

$^1$H NMR (300 MHz, C$_6$D$_6$, ppm) δ=0.34 (s, 3H, SiCH$_3$), 0.42 (s, 3H, SiCH$_3$), 1.05 (m, 1H, CH$_2$), 1.20 (m, 1H, CH$_2$), 1.22 (s, 9H, CH$_{3t-Bu}$), 1.27 (d, J$_{HH}$=6.8 Hz, 3H, CH$_{3i-Pr}$), 1.32 (d, J$_{HH}$=6.8 Hz, 3H, CH$_{3i-Pr}$), 1.38 (m, 2H, CH$_2$), 1.41 (s, 9H, CH$_{3t-Bu}$), 1.61 (m, 1H, CH$_2$), 1.75 (m, 1H, CH$_2$), 2.56 (d, J$_{HH}$=3.6 Hz, 1H, CH$_{bridgehead}$), 2.62 (d, J$_{HH}$=3.6 Hz, 1H, CH$_{bridgehead}$), 3.06 (m, 1H, CH), 3.09 (m, 1H, CH$_{iPr}$), 3.45 (sept., J$_{HH}$=6.8 Hz, 1H, CH$_{iPr}$), 7.11-7.24 (m, 3H, CH$_{Ar}$);

$^{13}$C{1H} (75 MHz, C$_6$D$_6$, ppm) δ=7.2 (s, SiCH$_3$), 7.5 (d, J$_{PC}$=1.7 Hz, SiCH$_3$), 22.3 (s, CH$_{3i-Pr}$), 23.1 (s, CH$_{3i-Pr}$), 24.5 (s, CH$_{i-Pr}$), 24.9 (s, CH$_{3i-Pr}$), 25.1 (s, CH$_2$), 27.9 (d, J$_{PC}$=3.6 Hz, CH$_{i-pr}$), 28.5 (s, CH$_{3i-Pr}$), 30.5 (s, CH$_2$), 32.3 (d, J$_{PC}$=5.9 Hz, CH$_{3t-Bu}$) 32.4 (d, J$_{PC}$=7.4 Hz, CH$_{3t-Bu}$), 37.3 (s, CH$_2$), 40.2 (s, CH$_{bridgehead}$), 42.1 (s, CH$_{bridgehead}$), 51.0 (d, $J_{PC}$=15.7 Hz, $C_{t-Bu}$), 51.6 (d, $J_{PC}$=8.0 Hz, $C_{t-Bu}$), 66.4 (d, $J_{PC}$=59.8 Hz, PCH), 122.7 (s, $CH_{ar}$), 123.2 (s, $CH_{ar}$), 123.4 (s, $CH_{ar}$), 136.7 (d, $J_{PC}$=1.3 Hz, $C_{ar}$), 136.8 (d, $J_{PC}$=0.9 Hz, $C_{ar}$), 148.0 (s, $C_{ar}$), 180.6 (d, $J_{PC}$=10.3 Hz, C=N);
$^{31}$PNMR {$^{1}$H} (121 MHz, $C_6D_6$, ppm) δ=147.3;
$^{29}$Si NMR {$^{1}$H} δ=(59 MHz, $C_6D_6$, ppm) 19.1 (d, $J_{PSi}$=3.7 Hz).

Synthesis of Compound 11

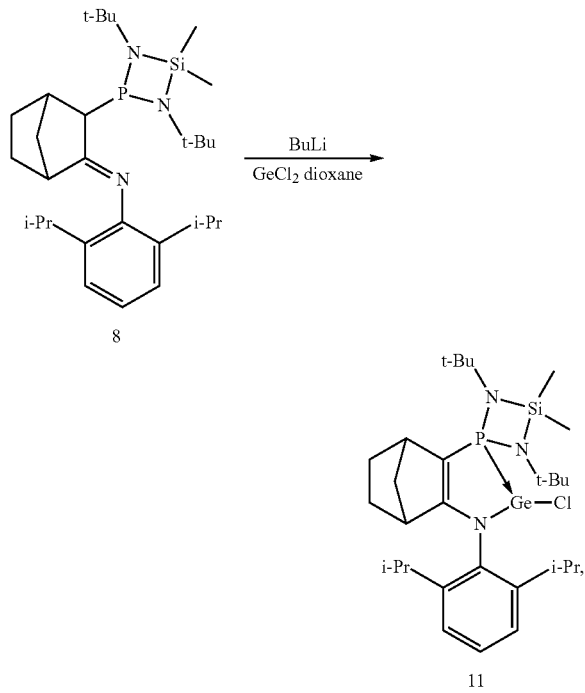

To a stirred solution of compound 8 prepared previously (5.0 g, 10 mmol) in 40 ml of THF cooled to −78° C. was added nBuLi (1.6 M, 6.9 mL, 11 mmol) and this mixture was then left to warm to room temperature over 1 hour with stirring. The solution was again cooled to −78° C. and a solution of germanium dichloride-dioxane complex prepared previously (2.32 g, 10 mmol) in THF (10 mL) was added. The mixture was left to warm to room temperature over 2 hours and the solvent was evaporated off under vacuum. The solid was taken up in 40 mL of toluene and filtered off The filtrate was concentrated to dryness and the resulting solid was washed twice with pentane (2×20 mL). The volatile substances were removed to give compound 11 (5.7 g, 94%) in the form of a white solid.

NMR Analysis of Compound 11:
Major Isomer of Compound 11 (64%)
$^{1}$H-NMR (300 MHz, $C_6D_6$, 25° C.) δ=0.22 (s, 3H, $SiCH_3$), 0.27 (s, 3H, $SiCH_3$), 1.17 (s, 9H, $CH_{3tBu}$), 1.19 (d, $J_{HH}$=9.1 Hz, 1H, $CH_2$), 1.24 (d, $J_{HH}$=6.7 Hz, 3H, $CH_{3iPr}$), 1.29 (d, $J_{HH}$=6.7 Hz, 3H, $CH_{3iPr}$), 1.29 (d, $J_{HH}$=7.1 Hz, 1H, $CH_2$), 1.33 (d, $J_{HH}$=7.1 Hz, 1H, $CH_2$), 1.38 (d, $J_{HH}$=6.7 Hz, 3H, $CH_{3iPr}$), 1.39 (s, 9H, $CH_{3tBu}$), 1.60 (d, $J_{HH}$=6.0 Hz, 3H, $CH_{3iPr}$), 1.64 (m, 2H, $CH_2$), 1.67 (d, $J_{HH}$=9.1 Hz, 1H, $CH_2$), 2.58 (b, 1H, $CH_{bridgehead}$), 3.05 (b, 1H, $CH_{bridgehead}$), 3.47 (sept., $J_{HH}$=6.9 Hz, 1H, $CH_{iPr}$), 3.68 (sept., $J_{HH}$=6.9 Hz, 1H, $CH_{iPr}$), 7.13-7.23 (m, 3H, $CH_{Ar}$);
$^{13}$C{$^{1}$H}-NMR (75 MHz, $C_6D_6$, 25° C.) δ=3.6 (d, $J_{PC}$=1.3 Hz, $SiCH_3$), 5.5 (d, $J_{PC}$=5.0 Hz, $SiCH_3$), 24.3 (s, $CH_{3iPr}$), 24.6 (s, $CH_{3iPr}$), 25.2 (d, $J_{PC}$=1.3 Hz, $CH_2$), 25.5 (s, $CH_{3iPr}$), 26.1 (d, $J_{PC}$=2.1 Hz, $CH_{3iPr}$), 27.7 (s, $CH_{iPr}$), 28.4 (s, $CH_{iPr}$), 29.0 (d, $J_{PC}$1.5 Hz, $CH_2$), 32.7 (d, $J_{PC}$3.0 Hz, $CH_{3tBu}$), 32.8 (d, $J_{PC}$=4.2 Hz, $CH_{3tBu}$), 40.6 (d, $J_{PC}$=7.0 Hz, $CH_{bridgehead}$), 43.8 (d, $J_{PC}$=14 Hz, $CH_{bridgehead}$), 46.5 (d, $J_{PC}$=5.2 Hz, $CH_2$), 51.0 (d, $J_{PC}$=2.9 Hz, $C_{tBu}$), 51.5 (d, $J_{PC}$=3.0 Hz, $C_{tBu}$), 98.9 (d, $J_{PC}$=21 Hz, PC), 123.7 (s, $CH_{Ar}$), 124.2 (s, $CH_{Ar}$), 126.7 (s, $CH_{Ar}$), 139.1 (d, $J_{PC}$=3.9 Hz, $C_{Ar}$), 145.5 (s, $C_{Ar}$), 147.5 (s, $C_{Ar}$), 184.6 (d, $J_{PC}$=42 Hz, NC);
$^{31}$P{$^{1}$H}-NMR (121 MHz, $C_6D_6$, 25° C.) δ=83.6 (s);
$^{29}$Si{$^{1}$H}-NMR (59 MHz, $C_6D_6$, 25° C.) δ=11.1 (d, $J_{PSi}$=4.1 Hz).

Minor Isomer of Compound 11 (36%)
$^{1}$H-NMR (300 MHz, $C_6D_6$, 25° C.) δ=0.23 (s, 3H, $SiCH_3$), 0.27 (s, 3H, $SiCH_3$), 1.20 (s, 9H, $CH_{3tBu}$), 1.22 (d, $J_{HH}$=9.0 Hz, 1H, $CH_2$), 1.24 (d, $J_{HH}$=6.6 Hz, 3H, $CH_{3iPr}$), 1.30 (d, $J_{HH}$=6.9 Hz, 3H, $CH_{3iPr}$), 1.34 (d, $J_{HH}$=6.9 Hz, 1H, $CH_2$), 1.35 (d, $J_{HH}$=7.0 Hz, 1H, $CH_2$), 1.39 (d, $J_{HH}$=6.9 Hz, 3H, $CH_{3iPr}$), 1.41 (s, 9H, $CH_{3tBu}$), 1.61 (d, $J_{HH}$=6.3 Hz, 3H, $CH_{3iPr}$), 1.58-1.71 (m, 3H, $CH_2$), 2.40 (b, 1H, $CH_{bridgehead}$), 3.05 (b, 1H, $CH_{bridgehead}$), 3.22 (sept., $J_{HH}$=6.9 Hz, 1H, $CH_{iPr}$), 4.00 (sept., $J_{HH}$=6.9 Hz, 1H, $CH_{iPr}$), 7.13-7.27 (m, 3H, $CH_{Ar}$);
$^{13}$C{$^{1}$H}-NMR (75 MHz, $C_6D_6$, 25° C.) δ=3.9 (d, $J_{PC}$=1.3 Hz, $SiCH_3$), 5.5 (d, $J_{PC}$=5.0 Hz, $SiCH_3$), 23.9 (s, $CH_{3iPr}$), 25.2 (s, $CH_{3iPr}$), 25.4 (s, $CH_{3iPr}$), 25.6 (d, $J_{PC}$=1.3 Hz, $CH_2$), 26.1 (d, $J_{PC}$=2.1 Hz, $CH_{3iPr}$), 27.6 (s, $CH_{iPr}$), 28.4 (s, $CH_{iPr}$), 28.6 (d, $J_{PC}$=1.5 Hz, $CH_2$) 32.4 (d, $J_{PC}$=4.0 Hz, $CH_{3tBu}$), 32.9 (d, $J_{PC}$=2.9 Hz, $CH_{3tBu}$), 40.6 (d, $J_{PC}$=7.0 Hz, $CH_{bridgehead}$), 43.3 (d, $J_{PC}$=14 Hz, $CH_{bridgehead}$), 48.7 (d, $J_{PC}$=6.0 Hz, $CH_2$), 51.5 (d, $J_{PC}$=3.9 Hz, 2C, $C_{tBu}$), 98.9 (d, $J_{PC}$=21 Hz, PC), 123.7 (s, $CH_{Ar}$), 124.4 (s, $CH_{Ar}$), 126.8 (s, $CH_{Ar}$), 139.5 (s, $C_{Ar}$), 145.9 (s, $C_{Ar}$), 147.8 (s, $C_{Ar}$), 184.5 (d, $J_{PC}$=23 Hz, NC);
$^{31}$P{$^{1}$H}-NMR (121 MHz, $C_6D_6$, 25° C.) δ=84.4 (s);
$^{29}$Si{$^{1}$H}-NMR (59 MHz, $C_6D_6$, 25° C.) δ=11.0 (d, $J_{PSi}$=4.3 Hz).

Synthesis of Compound C1

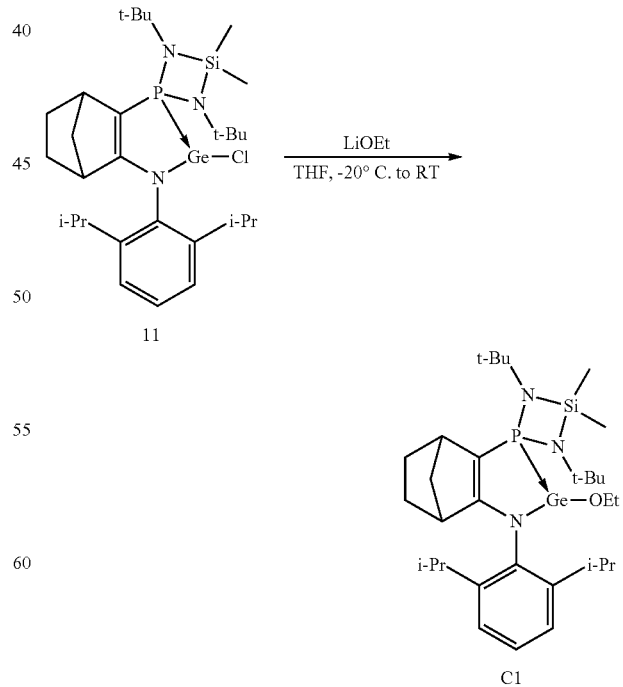

A freshly prepared solution of $LiOC_2H_5$ (106 mg, 2.0 mmol) in THF (5 mL) was added dropwise to a stirred solution of chlorogermylene 11 (1.125 g, 1.85 mmol) and tetrahydrofuran (THF) (10 mL) cooled in a cold bath at −60° C. The reaction mixture was stirred for 30 minutes at −60° C. After removing the cold bath, the reaction mixture was stored at room temperature for a further 30 minutes. The volatile substances were removed under vacuum and the residue was extracted with pentane (20 mL). The filtrate was concentrated to about 3 mL to perform crystallization in a freezer at −30° C.

Compound C1 is obtained in the form of white crystals by filtration, in a yield of 88% (1.0 g).

NMR Analysis of Compound C1:

Major Isomer of Compound C1 (64%)

$^1$-HNMR (300 MHz, $C_6D_6$, 25° C.) δ=0.29 (s, 3H, $Si(CH_3)_2$), 0.31 (s, 3H, $Si(CH_3)_2$), 1.11 (t, $^3J_{HH}$=6.9 Hz, 3H, $CH_3$), 1.25 (b, 1H, $CH_2$), 1.28 (s, 9H, $CH_{3tBu}$), 1.30 (m, 3H, $CH_{3iPr}$), 1.34 (s, 9H, $CH_{3tBu}$), 1.38 (m, 3H, $CH_{3iPr}$), 1.43 (m, 3H, $CH_{3iPr}$), 1.46 (b, 2H, $CH_2$) 1.51 (m, 3H, $CH_{3iPr}$), 1.68 (b, 1H, $CH_2$), 2.57 (b, 1H, $CH_{bridgehead}$), 3.10 (b, 1H, $CH_{bridgehead}$), 3.70 (m, 1H, $CH_{iPr}$), 3.84 (m, 1H, $CH_{iPr}$), 3.85 (m, 2H, $CH_2$), 7.08-7.26 (m, 3H, $CH_{Ar}$).

$^{13}C\{^1H\}$-NMR (75 MHz, $C_6D_6$, 25° C.) δ=4.05 (d, $J_{PC}$=1.4 Hz $Si(CH_3)_2$), 5.54 (d, $J_{PC}$=5.4 Hz, $Si(CH_3)_2$), 20.10 (s, $CH_3$), 24.35 (s, $CH_3iPr$), 24.35 (s, $CH_{3iPr}$), 24.7 (s, $CH_{3iPr}$), 25.36 (d, $J_{PC}$=3.5 Hz, $CH_2$), 26.13 (d, $J_{PC}$=2.8 Hz, $CH_{3iPr}$), 27.64 (s, $CH_{iPr}$), 28.24 (s, $CH_{iPr}$), 29.14 (d, $J_{PC}$=1.2 Hz, $CH_2$), 32.66 (d, $J_{PC}$=4.6 Hz, $CH_{3tBu}$), 32.79 (d, $J_{PC}$=2.7 Hz, $CH_{3tBu}$), 40.35 (d, $J_{PC}$=7.7 Hz, $CH_{bridgehead}$), 43.64 (d, $J_{PC}$=11.8 Hz, $CH_{bridgehead}$), 46.09 (d, $J_{PC}$=3.7 Hz, $CH_2$), 50.86 (d, $J_{PC}$=4.4 Hz, $C_{tBu}$), 50.98 (d, $J_{PC}$=3.6 Hz, $C_{tBu}$), 60.80 (d, $J_{PC}$=4.6 Hz, $OCH_2$), 97.58 (d, $J_{PC}$=13.7 Hz, PCCN), 123.43 (s, $CH_{Ar}$), 123.68 (s, $CH_{Ar}$), 126.03 (s, $CH_{Ar}$), 140.32 (d, $J_{PC}$=2.9 Hz, $C_{Ar}$), 145.65 (s, $C_{Ar}$), 147.53 (s, $C_{Ar}$), 183.19 (d, $J_{PC}$=36.5 Hz, PCCN).

$^{31}P\{^1H\}$-NMR (121 MHz, $C_6D_6$, 25° C.) δ=80.18 (s).

$^{29}Si\{^1H\}$-NMR (60 MHz, $C_6D_6$, 25° C.) δ=6.74 (d, $J_{PC}$=4.2 Hz).

Minor Isomer of Compound C1 (64%)

$^1$H-NMR (300 MHz, $C_6D_6$, 25° C.) δ=0.29 (s, 3H, $Si(CH_3)_2$), 0.31 (s, 3H, $Si(CH_3)_2$), 1.11 (t, $^3J_{HH}$=6.9 Hz, 3H, $CH_3$), 1.25 (b, 1H, $CH_2$), 1.28 (s, 9H, $CH_{3tBu}$), 1.30 (m, 3H, $CH_{3iPr}$), 1.34 (s, 9H, $CH_3tBu$), 1.38 (m, 3H, $CH_{3iPr}$), 1.43 (m, 3H, $CH_{3iPr}$), 1.46 (b, 2H, $CH_2$), 1.51 (m, 3H, $CH_{3iPr}$), 1.74 (m, 2H, $CH_2$), 2.45 (b, 1H, $CH_{bridgehead}$), 3.07 (b, 1H, $CH_{bridgehead}$), 3.38 (sept., $J_{HH}$=6.9 Hz, 1H, $CH_{iPr}$), 3.85 (m, 2H, $CH_2$), 4.03 (sept., J=6.9 Hz, 1H, $CH_{iPr}$), 7.09-7.26 (m, 3H, $CH_{Ar}$).

$^{13}C\{^1H\}$-NMR (75 MHz, $C_6D_6$, 25° C.) δ=4.25 (d, $J_{PC}$=1.4 Hz $Si(CH_3)_2$), 5.62 (d, $J_{PC}$=5.4 Hz, $Si(CH_3)_2$), 20.16 (s, $CH_3$), 23.76 (s, $CH_{3iPr}$), 24.35 (s, $CH_{3iPr}$), 25.02 (s, $CH_{3iPr}$), 25.62 (s, $CH_2$), 26.34 (d, $J_{PC}$=1.8 Hz, $CH_{3iPr}$), 27.35 (s, $CH_{iPr}$), 28.17 (s, $CH_{iPr}$), 28.90 (d, $J_{PC}$=1.3 Hz, $CH_2$), 32.06 (d, $J_{PC}$=4.7 Hz, $CH_{3tBu}$), 32.99 (d, $J_{PC}$=2.9 Hz, $CH_{3tBu}$), 40.53 (d, $J_{PC}$=7.6 Hz, $CH_{bridgehead}$), 43.28 (d, $J_{PC}$=13.2 Hz, $CH_{bridgehead}$), 48.28 (d, $J_{PC}$=5.1 Hz, $CH_2$), 50.98 (d, $J_{PC}$=3.6 Hz, $C_{tBu}$), 51.09 (d, $J_{PC}$=4.6 Hz, $C_{tBu}$), 60.80 (d, $J_{PC}$=4.6 Hz, $OCH_2$), 99.69 (d, $J_{PC}$=13.5 Hz, PCCN), 123.54 (s, $CH_{Ar}$), 123.74 (s, $CH_{Ar}$), 126.17 (s, $CH_{Ar}$), 141.02 (d, $J_{PC}$=2.9 Hz, $C_{Ar}$), 146.11 (s, $C_{Ar}$), 147.60 (s, $C_{Ar}$), 183.07 (d, $J_{PC}$=38.1 Hz, PCCN).

$^{31}P\{^1H\}$-NMR (121 MHz, $C_6D_6$, 25° C.) δ=81.58 (s).

$^{29}Si\{^1H\}$-NMR (60 MHz, $C_6D_6$, 25° C.) δ=6.98 (d, $J_{PC}$=4.1 Hz).

Example 2: Synthesis of a Compound C2 of Formula 1

Compound C2 was synthesized, having the formula:

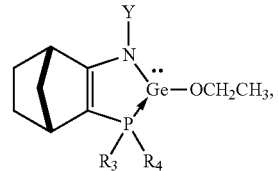

in which
Y is 2,4,6-trimethyl-$C_6H_2$, and
the phosphine group is represented by the formula:

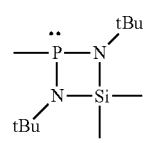

in which tBu is the tert-butyl group.

Synthesis of the Germanium Dichloride—Dioxane Complex

This compound is prepared according to the protocol described in Example 1.

Synthesis of Compound 3

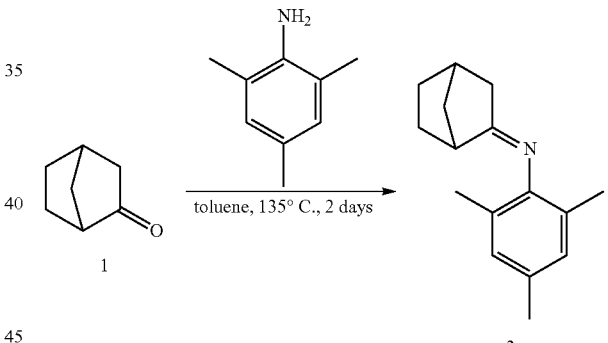

Norcamphor 1 (22.3 g, 0.2 mol), 2,4,6-trimethylaniline (28 ml, 0.2 mol), a catalytic amount of para-toluenesulfonic acid (0.38 g) and toluene (100 ml) were placed in a 250 ml two-necked round-bottomed flask equipped with a condenser and Dean-Stark apparatus. The mixture was heated at reflux for 4 days at 135° C. (oil bath temperature). The solvent was evaporated off and the oil was taken up in pentane and filtered to remove a small amount of precipitate. The solution was concentrated to dryness, to give compound 3 in the form of a yellow oil.

NMR Analysis of Compound 3:

Isomer $3_1$:

$^1$H-NMR (300 MHz, $C_6D_6$, 25° C.) δ=1.32-1.39 (m, 1H, $CH_2$), 1.50-1.56 (m, 2H, $CH_2$), 1.64-1.68 (m, 1H, $CH_2$), 1.72-1.80 (m, 3H, $CH_2$), 1.86-1.92 (m, 1H, $CH_2$), 2.03 (s, 6H, $CH_3$), 2.28 (s, 3H, $CH_3$), 2.51 (m, 1H, CHtdp), 3.05 (m, 1H, CHtdp), 6.85 (br s, 2H, CHAr);

$^{13}C\{^1H\}$-NMR (75 MHz, $C_6D_6$, 25° C.) δ=17.4 (s, $CH_3$), 17.5 (s, CH3), 20.6 (s, $CH_3$), 26.6 (s, $CH_2$), 27.5 (s, $CH_2$), 35.6 (s, CHtdp), 38.3 (s, $CH_2$), 39.1 (s, $CH_2$), 46.9 (s, CHtdp), 125.4 (s, CAr), 125.8 (s, CAr), 128.4 (s, CHAr), 128.5 (s, CHAr), 131.6 (s, CAr), 146.1 (s, CAr), 182.2 (s, C=N)

Isomer $3_2$:

$^1$H-NMR (300 MHz, C$_6$D$_6$, 25° C.) δ=1.32-1.39 (m, 1H, CH$_2$), 1.42-1.46 (m, 2H, CH$_2$), 1.50-1.56 (m, 1H, CH$_2$), 1.64-1.68 (m, 1H, CH$_2$), 1.76-1.78 (m, 1H, CH$_2$), 2.04 (s, 3H, CH$_3$), 2.10 (s, 3H, CH$_3$), 2.19 (m, 1H, CH$_2$), 2.25 (m, 1H, CH$_2$), 2.30 (s, 3H, CH$_3$), 2.51 (m, 1H, CHtdp), 2.61 (m, 1H, CHtdp), 6.86 (br s, 2H, CHAr); $^{13}$C{$^1$H}-NMR (75 MHz, C$_6$D$_6$, 25° C.) δ=17.9 (s, CH$_3$), 18.1 (s, CH$_3$), 20.6 (s, CH$_3$), 24.9 (s, CH$_2$), 27.6 (s, CH$_2$), 35.2 (s, CHtdp), 38.2 (s, CH$_2$), 41.5 (s, CH$_2$), 42.0 (s, CHtdp), 125.5 (s, CAr), 126.4 (s, CAr), 128.3 (s, CHAr), 128.3 (s, CHAr), 131.6 (s, CAr), 146.8 (s, CAr), 181.5 (s, C=N).

Synthesis of Compound 5

This compound is prepared according to the protocol described in Example 1.

Synthesis of Compound 9

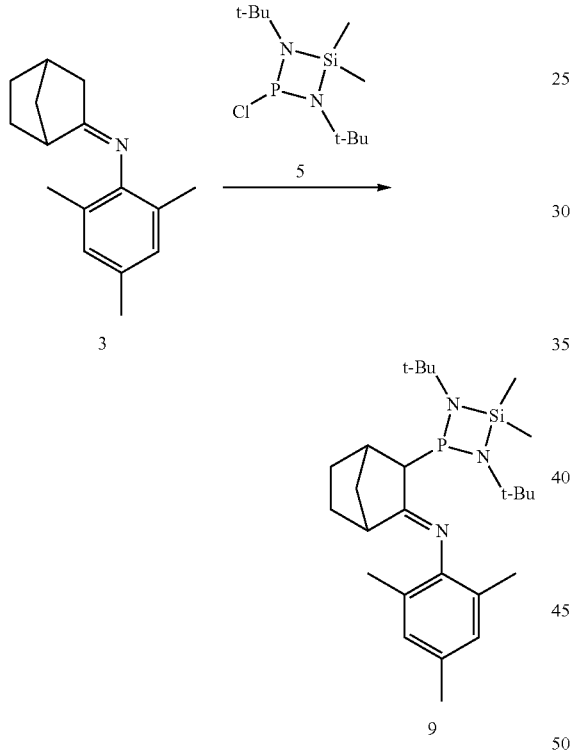

To a stirred solution of compound 3 (11.7 g, 51.46 mmol) in 70 ml of THF at −78° C. was added nBuLi (1.6 M, 34 mL, 54 mmol) and the mixture was then left to warm to room temperature over 1 hour with stirring. The solution was cooled to −78° C. and compound 5 (12.5 g, 46.8 mmol) was added. The mixture was left to warm to room temperature and the solvent was evaporated off under vacuum. The solid was washed with acetonitrile (three times, 80 ml), dried and dissolved with pentane, and then filtered. The volatile substances were removed to give compound 9 (19.7 g, 92%) in the form of a white solid.

NMR Analysis of Compound 9:

$^1$-NMR (300 MHz, C$_6$D$_6$, 25° C.) δ=0.37 (s, 3H, CH$_{3Si}$), 0.41 (s, 3H, CH$_{3Si}$), 1.00-1.05 (m, 1H, CH$_2$), 1.21 (s, 9H, CH$_{3t\text{-}Bu}$), 1.28-1.32 (m, 3H, CH$_2$), 1.37 (s, 9H, CH$_{3t\text{-}Bu}$), 1.60 (m, 1H, CH$_2$), 1.72-1.75 (m, 1H, CH$_2$), 2.21 (s, 9H, CH$_3$), 2.47 (m, 1H, PCCH$_{bridgehead}$), 2.57 (d, J$_{PH}$=3.6 Hz, 1H, PCH), 3.04 (m, 1H, NCCH$_{bridgehead}$), 6.83 (s, 2H, CH$_{Ar}$);

$^{13}$C{$^1$H}-NMR (75 MHz, C$_6$D$_6$, 25° C.) δ=7.0 (s, CH$_{3Si}$), 7.2 (d, J$_{PC}$=2.0 Hz, CH$_{3Si}$), 20.6 (s, 3C, CH$_3$), 25.6 (s, CH$_2$), 30.3 (s, CH$_2$), 32.2 (d, J$_{PC}$=6.2 Hz, 3C, CH$_{3t\text{-}Bu}$), 32.3 (d, J$_{PC}$=7.5 Hz, 3C, CH$_{3t\text{-}Bu}$), 37.0 (s, CH$_2$), 39.7 (s, NCCH$_{bridgehead}$), 42.1 (s, PCCH$_{bridgehead}$) 50.8 (d, J$_{PC}$=15.8 Hz, C$_{t\text{-}Bu}$), 51.4 (d, J$_{PC}$=8.3 Hz, C$_{t\text{-}Bu}$), 66.5 (d, J$_{PC}$=60.1 Hz, PCH), 128.6 (s, 2C, CH$_{Ar}$), 130.9 (s, 2C, C$_{Ar}$), 148.3 (s, C$_{Ar}$), 148.3 (s, C$_{Ar}$), 180.5 (d, J$_{PC}$=9.4 Hz, N=C);

$^{31}$P{$^1$H}-NMR (121 MHz, C$_6$D$_6$, 25° C.) δ=146.5;

$^{29}$Si{$^1$H}-NMR (59 MHz, C$_6$D$_6$, 25° C.) δ=18.6 (d, J$_{PSi}$=7.2 Hz).

Synthesis of Compound 12

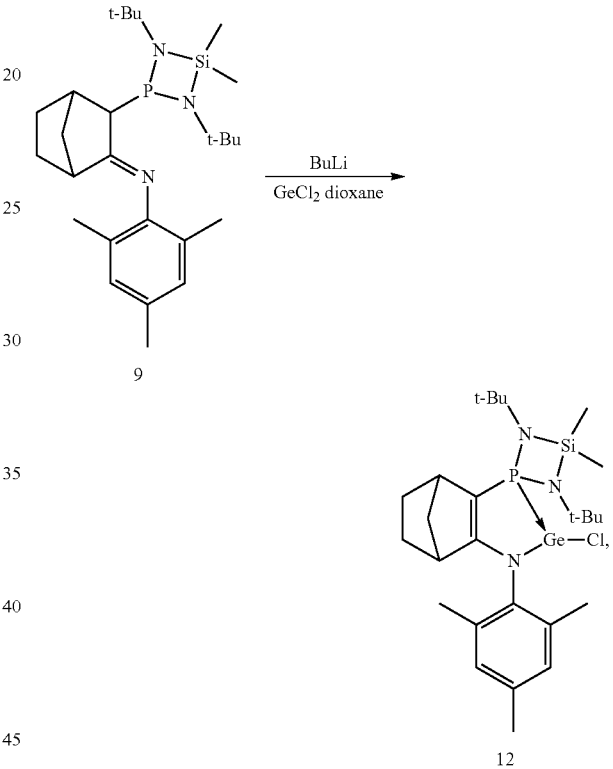

To a stirred solution of compound 9 prepared previously (4.5 g, 9.83 mmol) in 25 ml of THF cooled to −78° C. was added nBuLi (1.6 M, 6.45 mL, 10.32 mmol) and this mixture was then left to warm to room temperature over 1 hour with stirring. The solution was again cooled to −78° C. and a solution of germanium dichloride-dioxane complex prepared previously (2.28 g, 9.83 mmol) in THF (10 mL) was added. The mixture was left to warm to room temperature over 2 hours and the solvent was evaporated off under vacuum. The solid was taken up in 40 mL of toluene and filtered off The filtrate was concentrated to dryness and the resulting solid was washed twice with pentane (2×20 mL). The volatile substances were removed to give compound 12 (3.7 g, 86%) in the form of a yellowish solid.

NMR Analysis of Compound 12:

Major Isomer of Compound 12 (78%)

$^1$H-NMR (300 MHz, C$_6$D$_6$, 25° C.) δ=0.24 (s, 3H, CH$_{3Si}$), 0.28 (s, 3H, CH$_{3Si}$), 1.15 (d, J$_{PH}$=0.6 Hz, 9H, CH$_{3t\text{-}Bu}$), 1.13-1.2 (m, 2H, CH$_2$), 1.37 (d, J$_{PH}$=0.9 Hz, 9H, CH$_{3t\text{-}Bu}$), 1.57-1.71 (m, 3H, CH$_2$), 2.11 (m, 1H, CH$_2$), 2.17 (s, 3H, CH$_3$), 2.42 (s, 3H, CH$_3$), 2.53 (m, 1H, PCCH$_{tdp}$), 2.56 (s, 3H, CH$_3$), 3.02 (m, 1H, NCCH$_{tdp}$), 6.78-7.14 (s, 2H, CH$_{Ar}$);

$^{13}$C{$^1$H}-NMR (75 MHz, C$_6$D$_6$, 25° C.) δ=4.02 (d, J$_{PC}$=1.5 Hz, CH$_{3Si}$), 5.94 (d, J$_{PC}$=4.8 Hz, CH$_{3Si}$), 20.09 (s, CH$_3$), 20.47 (d, J$_{PC}$=2.5 Hz, CH$_3$), 21.03 (s, CH$_3$), 25.75 (s, CH$_2$), 29.49 (s, CH$_2$), 33.14 (d, J$_{PC}$=3.3 Hz, 3C, CH$_{3t\text{-}Bu}$), 33.23 (d, J$_{PC}$=4.4 Hz, 3C, CH$_{3t\text{-}Bu}$), 40.96 (d, J$_{PC}$=7.2 Hz, CH$_{bridgehead}$), 44.32 (d, J$_{PC}$=14.1 Hz, CH$_{bridgehead}$), 47.08 (d, J$_{PC}$=4.2 Hz, CH$_2$), 51.30 (d, J$_{PC}$=3.0 Hz, C$_{t\text{-}Bu}$), 51.87 (d, J$_{PC}$=3.6 Hz, C$_{t\text{-}Bu}$), 99.25 (d, J$_{PC}$=19.2 Hz, PC), 129.57 (s, CH$_{Ar}$), 130.05 (s, CH$_{Ar}$), 134.42 (s, C$_{Ar}$), 134.80 (s, 2C, C$_{Ar}$), 136.62 (s, C$_{Ar}$), 185.17 (d, J$_{PC}$=42.0 Hz, NC);

$^{31}$P{$^1$H}-NMR (121 MHz, C$_6$D$_6$, 25° C.) δ=83.02;

$^{29}$Si{$^1$H}-NMR (59 MHz, C$_6$D$_6$, 25° C.) δ=11.44 (d, J$_{PSi}$=4.1 Hz).

Minor Isomer of Compound 12 (22%)

$^1$H-NMR (300 MHz, C$_6$D$_6$, 25° C.) δ=0.25 (s, 3H, CH$_{3Si}$), 0.29 (s, 3H, CH$_{3Si}$), 1.20-1.25 (m, 2H, CH$_2$), 1.21 (d, J$_{PH}$=0.3 Hz, 9H, CH$_{3t\text{-}Bu}$), 1.43 (d, J$_{PH}$=0.6 Hz, 9H, CH$_{3t\text{-}Bu}$), 1.45-1.60 (m, 3H, CH$_2$), 2.11 (m, 1H, CH$_2$), 2.16 (s, 3H, CH$_3$), 2.29 (s, 3H, CH$_3$), 2.35 (m, 1H, PCCH$_{tdp}$), 2.65 (s, 3H, CH$_3$), 3.02 (m, 1H, NCCH$_{tdp}$), 6.78-7.14 (m, 2H, CH$_{Ar}$);

$^{13}$C{$^1$H}-NMR (75 MHz, C$_6$D$_6$, 25° C.) δ=4.32 (d, J$_{PC}$=1.7 Hz, CH$_{3Si}$), 5.86 (d, J$_{PC}$=5.3 Hz, CH$_{3Si}$), 19.80 (d, J$_{PC}$=1.0 Hz, CH$_3$), 20.23 (s, CH$_3$), 21.03 (s, CH$_3$), 25.67 (s, CH$_2$), 28.95 (s, CH$_2$), 32.90 (d, J$_{PC}$=4.9 Hz, 3C, CH$_{3t\text{-}Bu}$), 33.48 (d, J$_{PC}$=3.1 Hz, 3C, CH$_{3t\text{-}Bu}$), 40.96 (d, J$_{PC}$=7.2 Hz, CH$_{bridgehead}$), 43.82 (d, J$_{PC}$=14.0 Hz, CH$_{bridgehead}$), 49.41 (d, J$_{PC}$=3.1 Hz, CH$_2$), 51.30 (d, J$_{PC}$=3.0 Hz, C$_{t\text{-}Bu}$), 51.89 (d, J$_{PC}$=2.4 Hz, C$_{t\text{-}Bu}$), 101.25 (d, J$_{PC}$=18.8 Hz, PC), 129.17 (s, CH$_{Ar}$), 130.20 (s, CH$_{Ar}$), 135.04 (s, C$_{Ar}$), 135.18 (s, C$_{Ar}$), 136.83 (s, C$_{Ar}$), 140.54 (d, J$_{PC}$=3.0 C$_{Ar}$), 184.46 (d, J$_{PC}$=38.5 Hz, NC);

$^{31}$P{$^1$H}-NMR (121 MHz, C$_6$D$_6$, 25° C.) δ=84.26;

$^{29}$Si{$^1$H}-NMR (59 MHz, C$_6$D$_6$, 25° C.) δ=11.07 (d, J$_{PSi}$=4.1 Hz).

Synthesis of Compound C2

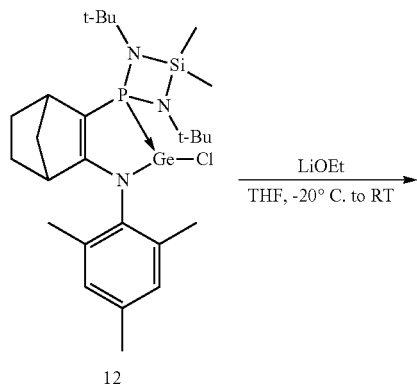

12

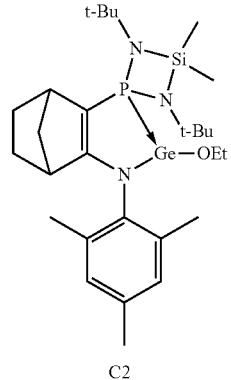

C2

A freshly prepared solution of LiOC$_2$H$_5$ (56 mg, 1.08 mmol) in THF (5 mL) was added dropwise to a stirred solution of compound 12 (0.58 g, 1.02 mmol) and tetrahydrofuran (THF) (10 mL) cooled in a cold bath at −10° C. The reaction mixture was stirred for 30 minutes at −10° C. and the cold bath was then removed. The reaction mixture was left to warm to room temperature for a further 30 minutes. The volatile substances were removed under vacuum and the residue was extracted with pentane (20 mL).

The filtrate was concentrated to dryness to obtain compound C2 (0.55 g, 94%) in the form of a sufficiently pure amorphous solid.

NMR Analysis of Compound C2:

Major Isomer of Compound C2 (64%)

$^1$H-NMR (300 MHz, C$_6$D$_6$, 25° C.) δ=0.29 (s, 3H, CH$_{3Si}$), 0.31 (s, 3H, CH$_{3Si}$), 1.13 (d, J$_{PH}$=6.9 Hz, 3H, CH$_3$), 1.27 (b, 9H, CH$_{3t\text{-}Bu}$), 1.30 (m, 2H, CH$_2$), 1.40 (b, 9H, CH$_{3t\text{-}Bu}$), 1.60-1.78 (m, 3H, CH$_2$), 2.19 (s, 3H, CH$_3$), 2.23 (m, 1H, CH$_2$), 2.51 (s, 3H, CH$_3$), 2.54 (m, 1H, PCCH$_{tdp}$), 2.57 (s, 3H, CH$_3$), 3.07 (m, 1H, NCCH$_{tdp}$), 3.76-3.98 (m, 2H, CH$_2$), 6.92 (s, 1H, CH$_{Ar}$), 7.16 (s, 1H, CH$_{Ar}$);

$^{13}$C{$^1$H}-NMR (75 MHz, C$_6$D$_6$, 25° C.) δ=4.31 (d, J$_{PC}$=1.7 Hz, CH$_{3Si}$), 6.04 (d, J$_{PC}$=5.0 Hz, CH$_{3Si}$), 18.84 (s, CH$_3$), 19.83 (s, CH$_3$), 20.43 (s, CH$_3$), 21.09 (s, CH$_3$), 25.91 (s, CH$_2$), 29.38 (s, CH$_2$), 32.95 (d, J$_{PC}$=4.6 Hz, 3C, CH$_{3t\text{-}Bu}$), 33.13 (d, J$_{PC}$=3.1 Hz, 3C, CH$_{3t\text{-}Bu}$), 40.89 (d, J$_{PC}$=7.9 Hz, CH$_{bridgehead}$), 44.06 (d, J$_{PC}$=12.7 Hz, CH$_{bridgehead}$) 46.89 (d, J$_{PC}$=4.3 Hz, CH$_2$), 50.18 (d, J$_{PC}$=12.4 Hz, C$_{t\text{-}Bu}$), 51.18 (d, J$_{PC}$=3.6 Hz, C$_{t\text{-}Bu}$), 61.61 (d, J$_{PC}$=14.9 Hz, CH$_2$), 97.10 (d, J$_{PC}$=19.3 Hz, PC), 129.29 (s, CH$_{Ar}$), 129.34 (s, CH$_{Ar}$), 134.22 (s, C$_{Ar}$), 134.81 (s, C$_{Ar}$), 135.12 (s, C$_{Ar}$), 136.94 (s, C$_{Ar}$), 184.44 (d, J$_{PC}$=51.0 Hz, NC);

$^{31}$P{$^1$H}-NMR (121 MHz, C$_6$D$_6$, 25° C.) δ=77.89;

$^{29}$Si{$^1$H}-NMR (59 MHz, C$_6$D$_6$, 25° C.) δ=6.74 (d, J$_{PSi}$=4.1 Hz).

Minor Isomer of Compound C2 (36%)

$^1$H-NMR (300 MHz, C$_6$D$_6$, 25° C.) δ=0.28 (s, 3H, CH$_{3Si}$), 0.32 (s, 3H, CH$_{3Si}$), 1.22 (d, J$_{PH}$=6.9 Hz, 3H, CH$_3$), 1.26 (b, 9H, CH$_{3t\text{-}Bu}$), 1.32 (m, 2H, CH$_2$), 1.43 (s, 9H, CH$_{3t\text{-}Bu}$), 1.45-1.56 (m, 3H, CH$_2$), 2.16 (m, 1H, CH$_2$), 2.19 (s, 3H, CH$_3$), 2.38 (s, 3H, CH$_3$), 2.44 (b, 1H, PCCH$_{tdp}$), 2.65 (s, 3H, CH$_3$), 3.44 (m, 1H, NCCH$_{tdp}$), 3.76-3.98 (m, 2H, CH$_2$), 6.75 (s, 1H, CH$_{Ar}$), 6.84 (s, 1H, CH$_{Ar}$);

$^{13}$C{$^1$H}-NMR (75 MHz, C$_6$D$_6$, 25° C.) δ=4.58 (d, J$_{PC}$=1.6 Hz, CH$_{3Si}$), 7.76 (d, J$_{PC}$=5.4 Hz, CH$_{3Si}$), 19.72 (s, CH$_3$), 20.30 (s, CH$_3$), 20.57 (s, CH$_3$), 21.01 (s, CH$_3$), 26.82 (s, CH$_2$), 29.74 (s, CH$_2$), 32.55 (d, J$_{PC}$=5.0 Hz, 3C, CH$_{3t\text{-}Bu}$), 33.49 (d, J$_{PC}$=3.1 Hz, 3C, CH$_{3t\text{-}Bu}$), 41.05 (d, J$_{PC}$=7.7 Hz, CH$_{bridgehead}$), 43.74 (d, J$_{PC}$=13.1 Hz, CH$_{bridgehead}$), 48.82 (d, J$_{PC}$=5.4 Hz, CH$_2$), 50.58 (d, J$_{PC}$=11.2 Hz, C$_{t\text{-}Bu}$), 51.46

(d, $J_{PC}$=4.0 Hz, $C_{t-Bu}$), 61.41 (d, $J_{PC}$=14.2 Hz, $CH_2$), 99.16 (d, $J_{PC}$=13.3 Hz, PC), 129.29 (s, $CH_{Ar}$), 129.43 (s, $CH_{Ar}$), 134.44 (s, $C_{Ar}$), 135.35 (s, $C_{Ar}$), 136.13 (s, $C_{Ar}$), 137.05 (s, $C_{Ar}$), 183.05 (d, $J_{PC}$=48.1 Hz, NC);

$^{31}P\{^1H\}$-NMR (121 MHz, $C_6D_6$, 25° C.) δ=80.43;

$^{29}Si\{^1H\}$-NMR (59 MHz, $C_6D_6$, 25° C.) δ=6.98 (d, $J_{PSi}$=4.0 Hz).

Example 3: Synthesis of a Compound C3 of Formula 1

Compound C3 was synthesized, having the formula:

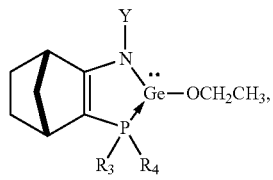

in which
Y is 2,6-iPr$_2$—C$_6$H$_3$, and
the phosphine group is represented by the formula:

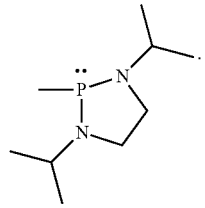

Synthesis of the Germanium Dichloride—Dioxane Complex

This compound is prepared according to the protocol described in Example 1.

Synthesis of Compound 2

This compound is prepared according to the protocol described in Example 1.

Synthesis of compound 7

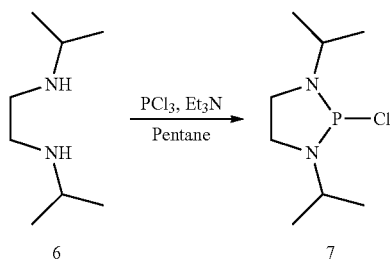

To a stirred solution of compound 6 (14.4 g, 0.10 mol) and triethanolamine (70 ml, 0.50 mol) in 60 ml of pentane cooled to 0° C. was added PCl$_3$ (8.75 mL, 0.10 mol) dropwise. The reaction mixture was stirred overnight (20 hours) at room temperature. The solution was filtered and the filter cake was washed twice with 100 ml of pentane. The combined filtrates were concentrated, and the residue obtained was distilled under vacuum to give compound 7 (12.3 g, 60%) in the form of a colorless oil.

NMR Analysis of Compound 7:

$^1H$-NMR (300 MHz, $C_6D_6$, 25° C.) δ=0.90 (d, $J_{HH}$=3.4 Hz, 12H, $CH_3$), 2.87 (b, 2H, CH), 2.97 (m, 4H, $CH_2$);

$^{13}C\{^1H\}$-NMR (75 MHz, $C_6D_6$, 25° C.) δ=21.4 (s, $CH_3$), 22.0 (s, $CH_3$), 46.7 (d, $J_{PC}$=10.4 Hz, $CH_2$), 48.0 (d, $J_{PC}$=14.9 Hz, CH);

$^{31}P\{^1H\}$-NMR (75 MHz, $C_6D_6$, 25° C.) δ=160.8.

Synthesis of Compound 10

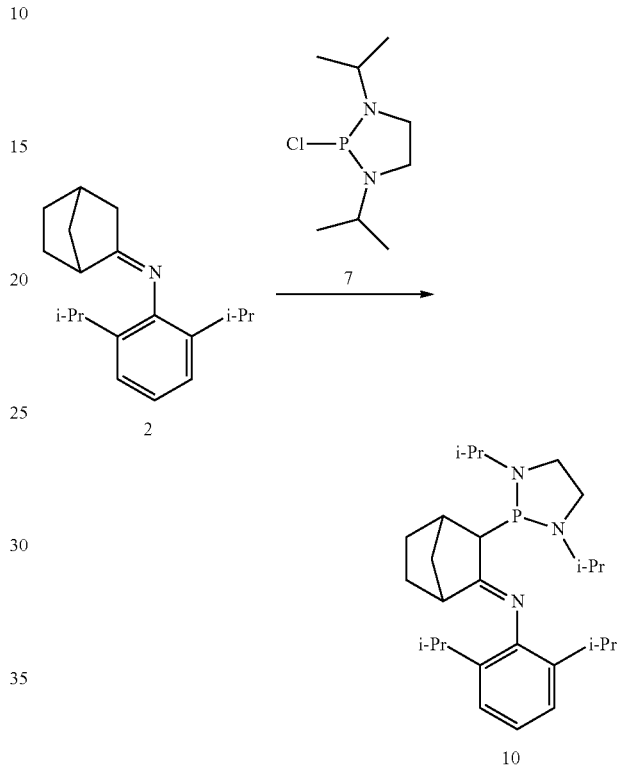

To a stirred solution of compound 2 prepared previously (16.03 g, 59.5 mmol) in 70 ml of THF at −78° C. was added nBuLi (1.6 M, 39 mL, 62.5 mmol) and this mixture was then left to warm to room temperature over 1 hour with stirring. The solution was again cooled to −78° C. and compound 7 prepared previously (12.3 g, 59.5 mmol) was added. The mixture was left to warm to room temperature over 2 hours and the solvent was evaporated off under vacuum. The solid was washed with acetonitrile (three times, 80 ml), dried and dissolved with pentane, and then filtered. The volatile substances were removed to obtain product 10 (20.2 g, 76%) in the form of a white solid.

NMR Analysis of Compound 10

$^1H$-NMR (300 MHz, $C_6D_6$, 25° C.) δ=1.03 (d, $J_{HH}$=2.1 Hz, 3H, $CH_{3i-Pr}$), 1.06 (b, 9H, $CH_{3i-Pr}$), 1.11 (b, 9H, $CH_{3i-Pr}$), 1.15 (d, $J_{HH}$=1.8 Hz, 3H, $CH_{3i-Pr}$), 1.22 (m, 2H, $CH_2$), 1.32 (m, 2H, $CH_2$), 1.68 (m, 2H, $CH_2$), 2.16 (d, $J_{HH}$=3.6 Hz, 1H, PCH), 2.46 (d, $J_{HH}$=9.6 Hz, 1H, $CH_{bridgehead}$), 2.56 (m, 1H, $CH_{bridgehead}$), 2.79 (sept, $J_{HH}$=9.6 Hz, 1H, $CH_{i-Pr}$), 2.91 (m, 1H, $CH_{i-Pr}$), 3.02 (m, 3H, $NCH_2$, $CH_{i-Pr}$), 3.20 (m, 2H, $NCH_2$), 3.41 (m, 1H, $CH_{i-Pr}$), 6.90-7.05 (m, 3H, $CH_{Ar}$);

$^{13}C\{^1H\}$-NMR (75 MHz, $C_6D_6$, 25° C.) δ=22.0 (d, $J_{PC}$=6.7 Hz, $CH_{3i-Pr}$), 22.2 (d, $J_{PC}$=6.5 Hz, $CH_{3i-Pr}$), 22.2 (s, $CH_{3i-Pr}$), 22.4 (d, $J_{PC}$=7.3 Hz, $CH_{3i-Pr}$), 22.8 (d, $J_{PC}$=13.8 Hz, $CH_{3i-Pr}$), 23.0 (s, $CH_{3i-Pr}$), 24.3 (s, $CH_{3i-Pr}$), 24.7 (s, $CH_{3i-Pr}$), 25.2 (d, $J_{PC}$=1.5 Hz, $CH_2$), 27.5 (d, $J_{PC}$=3.4 Hz,

CH$_{i-Pr}$), 28.3 (s, CH$_{i-Pr}$), 29.2 (d, J$_{PC}$=1.2 Hz, CH$_2$), 35.9 (d, J$_{PC}$=4.2 Hz, CH$_2$), 39.4 (d, J$_{PC}$=4.7 Hz, CH$_{i-Pr}$), 42.2 (s, CH$_{i-Pr}$), 45.6 (d, J$_{PC}$=8.8 Hz, CH$_2$), 48.2 (d, J$_{PC}$=7.2 Hz, CH$_2$), 49.0 (d, J$_{PC}$=20.7 Hz, CH$_{bridgehead}$), 52.2 (d, J$_{PC}$=26.0 Hz, CH$_{bridgehead}$), 55.6 (d, J$_{PC}$=42.1 Hz, PCH), 122.6 (s, CH$_{Ar}$), 123.1 (s, CH$_{Ar}$), 123.2 (s, CH$_{Ar}$), 136.2 (d, J$_{PC}$=1.7 Hz, C$_{Ar}$), 136.8 (d, J$_{PC}$=1.3 Hz, C$_{Ar}$), 147.9 (d, J$_{PC}$=1.4 Hz, C$_{Ar}$), 180.4 (d, J$_{PC}$=8.0 Hz, N=C);

$^{31}$P{$^1$H}-NMR (121 MHz, C$_6$D$_6$, 25° C.) δ=104.7.

Synthesis of Compound 13

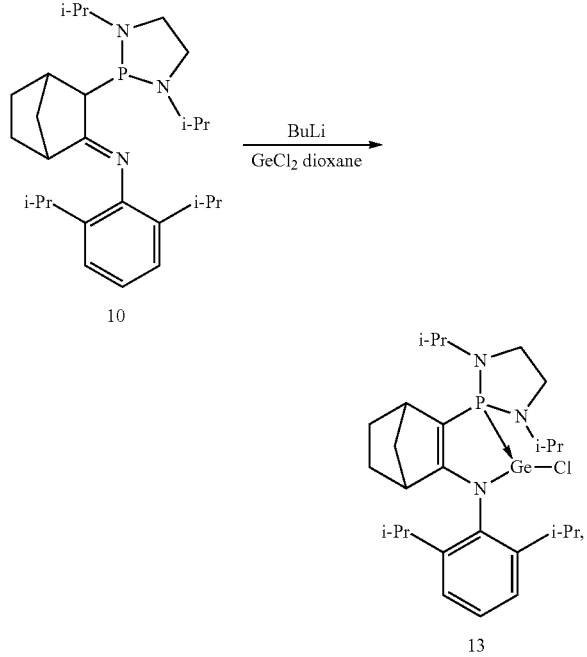

To a stirred solution of compound 10 prepared previously (3.0 g, 6.79 mmol) in 20 ml of THF cooled to −78° C. was added nBuLi (1.6 M, 4.4 mL, 7.1 mmol) and this mixture was then left to warm to room temperature over 1 hour with stirring. The solution was again cooled to −78° C. and a solution of germanium dichloride-dioxane complex prepared previously (1.6 g, 6.8 mmol) in THF (10 mL) was added. The mixture was left to warm to room temperature over 2 hours and the solvent was evaporated off under vacuum. The solid was taken up in 40 mL of toluene and filtered off. The filtrate was concentrated to dryness and the resulting solid was washed twice with pentane (2×20 mL). The volatile substances were removed to give compound 13 (3.7 g, 86%) in the form of a yellowish solid.

NMR analysis of compound 13:

Minor isomer of compound 13 (45%)

$^1$H-NMR (300 MHz, C$_6$D$_6$, 25° C.) δ=0.91 (d, J$_{HH}$=6.8 Hz, 3H, CH$_{3i-Pr}$), 0.93 (d, J$_{HH}$=6.1 Hz, 3H, CH$_{3i-Pr}$), 1.01 (d, J$_{HH}$=7.0 Hz, 3H, CH$_{3i-Pr}$), 1.19 (d, J$_{HH}$=7.1 Hz, 3H, CH$_{3i-Pr}$), 1.20 (m, 1H, CH$_2$), 1.26 (d, J$_{HH}$=7.4 Hz, 3H, CH$_{3i-Pr}$), 1.27 (d, J$_{HH}$=7.1 Hz, 3H, CH$_{3i-Pr}$), 1.29 (d, J$_{HH}$=5.8 Hz, 3H, CH$_{3i-Pr}$), 1.35 (b, 1H, CH$_2$), 1.50 (b, 2H, CH$_2$), 1.53 (d, J$_{HH}$=6.1 Hz, 3H, CH$_{3i-Pr}$), 1.68 (b, 1H, CH$_2$), 1.73 (b, 1H, CH$_2$), 2.32 (b, 1H, PCCH$_{td}$), 2.42-2.70 (m, 4H, NCH$_2$), 2.73 (b, 1H, NCCH$_{tdp}$), 3.14 (sept, J$_{HH}$=6.9 Hz, 1H, CH$_{i-Pr}$), 3.24 (m, 1H, CH$_{i-Pr}$), 3.70 (sept, J$_{HH}$=6.8 Hz, 1H, CH$_{i-Pr}$), 4.05 (m, 1H, CH$_{i-Pr}$), 7.07-7.22 (m, 3H, CH$_{Ar}$);

$^{13}$C{$^1$H}-NMR (75 MHz, C$_6$D$_6$, 25° C.) δ=20.3 (d, J$_{PC}$=2.1 Hz, CH$_{3i-Pr}$), 20.7 (s, CH$_{3i-Pr}$), 21.1 (d, J$_{PC}$=5.4 Hz, CH$_{3i-Pr}$), 22.2 (d, J$_{PC}$=4.3 Hz, CH$_{3i-Pr}$), 24.0 (s, CH$_{3i-Pr}$), 24.6 (s, CH$_{3i-Pr}$), 25.5 (s, CH$_2$), 25.9 (s, CH$_{3i-Pr}$), 26.2 (s, CH$_{3i-Pr}$), 27.8 (s, CH$_{i-Pr}$), 28.8 (s, CH$_{i-Pr}$), 29.6 (d, J$_{PC}$=0.8 Hz, CH$_2$), 38.7 (s, CH$_2$), 39.3 (d, J$_{PC}$=1.9 Hz, CH$_2$), 40.5 (d, J$_{PC}$=8.0 Hz, CH$_{tdp}$), 43.4 (d, J$_{PC}$=14.2 Hz, CH$_{tdp}$), 44.4 (d, J$_{PC}$=9.7 Hz, CH$_{i-Pr}$), 45.0 (d, J$_{PC}$=1.75 Hz, CH$_{i-Pr}$), 48.8 (d, J$_{PC}$=3.1 Hz, CH$_2$), 91.8 (d, J$_{PC}$=21.6 Hz, PC), 123.8 (s, CH$_{Ar}$), 124.5 (s, CH$_{Ar}$), 126.6 (s, CH$_{Ar}$), 140.3 (d, J$_{PC}$=5.7 Hz, C$_{Ar}$), 146.3 (s, C$_{Ar}$), 147.6 (s, C$_{Ar}$), 191.1 (d, J$_{PC}$=42.4 Hz, NC);

$^{31}$P{$^1$H}-NMR (121 MHz, C$_6$D$_6$, 25° C.) δ=71.3.

Major Isomer of Compound 13 (55%)

$^1$H-NMR (300 MHz, C$_6$D$_6$, 25° C.) δ=0.98 (d, J$_{HH}$=6.5 Hz, 3H, CH$_{3i-Pr}$), 1.00 (d, J$_{HH}$=7.1 Hz, 3H, CH$_{3i-Pr}$), 1.04 (d, J$_{HH}$=7.1 Hz, 3H, CH$_{3i-Pr}$), 1.18 (m, 1H, CH$_2$), 1.21 (d, J$_{HH}$=6.8 Hz, 3H, CH$_{3i-Pr}$), 1.24 (d, J$_{HH}$=7.1 Hz, 3H, CH$_{3i-Pr}$), 1.31 (d, J$_{HH}$=6.5 Hz, 3H, CH$_{3i-Pr}$), 1.34 (d, J$_{HH}$=7.1 Hz, 3H, CH$_{3i-Pr}$), 1.38 (b, 1H, CH$_2$), 1.40 (b, 1H, CH$_2$), 1.50 (d, J$_{HH}$=6.7 Hz, 3H, CH$_{3i-Pr}$), 1.52 (b, 1H, CH$_2$), 1.62 (b, 1H, CH$_2$), 1.68 (b, 1H, CH$_2$), 2.42-2.70 (m, 4H, CH$_2$), 2.60 (b, 1H, PCCH$_{tdp}$), 2.88 (b, 1H, NCCH$_{tdp}$), 3.26 (sept, J$_{HH}$=6.7 Hz, 1H, CH$_{i-Pr}$), 3.47 (m, 1H, CH$_{i-Pr}$), 3.99 (sept, J$_{HH}$=6.9 Hz, 1H, CH$_{i-Pr}$), 4.21 (m, 1H, CH$_{i-Pr}$), 7.07-7.22 (m, 3H, CH$_{Ar}$);

$^{13}$C{$^1$H}-NMR (75 MHz, C$_6$D$_6$, 25° C.) δ=20.4 (d, J$_{PC}$=0.7 Hz, CH$_{3i-Pr}$), 21.0 (d, J$_{PC}$=2.3 Hz, CH$_{3i-Pr}$), 21.3 (d, J$_{PC}$=5.6 Hz, CH$_{3i-Pr}$), 22.0 (d, J$_{PC}$=6.9 Hz, CH$_{3i-Pr}$), 24.2 (s, CH$_{3i-Pr}$), 24.4 (s, CH$_{3i-Pr}$), 25.4 (s, CH$_{3i-Pr}$), 25.5 (s, CH$_2$), 26.1 (d, J$_{PC}$=2.0 Hz, CH$_{3i-Pr}$), 27.9 (s, CH$_{i-Pr}$), 28.7 (s, CH$_{i-Pr}$), 29.6 (d, J$_{PC}$=1.2 Hz, CH$_2$), 38.7 (s, CH$_2$), 39.4 (d, J$_{PC}$=2.8 Hz, CH$_2$), 40.9 (d, J$_{PC}$=8.5 Hz, CH$_{tdp}$), 44.2 (d, J$_{PC}$=13.4 Hz, CH$_{tdp}$), 44.8 (d, J$_{PC}$=3.4 Hz, CH$_{i-Pr}$), 45.2 (d, J$_{PC}$=9.0 Hz, CH$_{i-Pr}$), 46.8 (d, J$_{PC}$=4.7 Hz, CH$_2$), 89.7 (d, J$_{PC}$=25.2 Hz, PC), 123.3 (s, CH$_{Ar}$), 124.4 (s, CH$_{Ar}$), 126.6 (s, CH$_{Ar}$), 139.5 (d, J$_{PC}$=4.1 Hz, C$_{Ar}$), 145.5 (s, C$_{Ar}$), 147.6 (s, C$_{Ar}$), 190.5 (d, J$_{PC}$=41.1 Hz, NC);

$^{31}$P{$^1$H}-NMR (121 MHz, C$_6$D$_6$, 25° C.) δ=65.2.

Synthesis of Compound C3

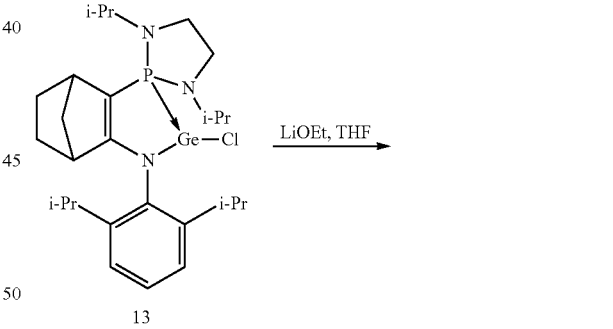

A freshly prepared solution of LiOC$_2$H$_5$ (227 mg, 4.37 mmol) in THF (5 mL) was added dropwise to a stirred solution of compound 13 prepared previously (2.0 g, 3.64 mmol) and THF (10 mL) cooled in a cold bath at −10° C. The reaction mixture was stirred for 30 minutes at −10° C. and the cold bath was then removed. The reaction mixture was left to warm to room temperature for a further 30 minutes. The volatile substances were removed under vacuum and the residue was extracted with pentane (20 mL).

The filtrate was concentrated to about 5 ml and stored in a freezer at −30° C. for crystallization. After filtration, 1.3 g of compound C3 (64% yield) were obtained in the form of white crystals.

NMR Analysis of Compound C3:

Major Isomer of Compound C3 (72%)

$^1$H-NMR (300 MHz, $C_6D_6$, 25° C.) δ=0.94 (d, $J_{HH}$=6.6 Hz, 3H, $CH_{3i-Pr}$), 1.05-1.13 (m, 9H, $CH_{3i-Pr}$), 1.19-1.29 (m, 2H, $CH_2$), 1.22-1.31 (m, 9H, $CH_{3i-Pr}$), 1.34-1.43 (m, 1H, $CH_2$), 1.40-1.48 (m, 9H, $CH_3$, $CH_{3i-Pr}$), 1.60-1.76 (m, 3H, $CH_2$), 2.56 (b, 1H, $CH_{bridgehead}$), 2.58-2.76 (m, 4H, $NCH_2$), 2.93 (b, 1H, $CH_{bridgehead}$), 3.41-4.04 (m, 6H, $OCH_2$, $CH_{i-Pr}$), 7.11-7.24 (m, 3H, $CH_{Ar}$); $^{13}C\{^1H\}$-NMR (75 MHz, $C_6D_6$, 25° C.) δ=20.45 (s, $CH_{3i-Pr}$), 21.20 (d, $J_{PC}$=3.7 Hz, $CH_{3i-Pr}$), 21.30 (d, $J_{PC}$=5.8 Hz, $CH_{3i-Pr}$), 21.99 (d, $J_{PC}$=5.5 Hz, $CH_{3i-Pr}$), 24.69 (s, $CH_{3i-Pr}$), 24.79 (s, $CH_{3i-Pr}$), 25.06 (s, $CH_{3i-Pr}$), 25.92 (s, $CH_2$), 26.32 (s, $CH_{3i-Pr}$), 28.26 (s, 2C, $CH_3$, $CH_{i-Pr}$), 28.75 (s, $CH_{i-Pr}$), 30.35 (d, $J_{PC}$=1.8 Hz, $CH_2$), 40.50 (d, $J_{PC}$=2.1 Hz, $CH_2$), 40.64 (s, $CH_2$), 41.23 (d, $J_{PC}$=8.9 Hz, $CH_{bridgehead}$), 44.18 (d, $J_{PC}$=11.2 Hz, $CH_{tdp}$), 45.18 (d, $J_{PC}$=7.3 Hz, $CH_{i-Pr}$), 45.45 (d, $J_{PC}$=10.0 Hz, $CH_{i-Pr}$), 46.56 (d, $J_{PC}$=3.4 Hz, $CH_2$), 62.02 (d, $J_{PC}$=13.6 Hz, $CH_2$), 91.18 (d, $J_{PC}$=19.1 Hz, PC), 123.89 (s, $CH_{Ar}$), 124.04 (s, $CH_{Ar}$), 126.34 (s, $CH_{Ar}$), 145.98 (s, $C_{Ar}$), 148.13 (s, 2C, $C_{Ar}$), 187.75 (d, $J_{PC}$=39.3 Hz, NC); $^{31}P\{^1H\}$-NMR (121 MHz, $C_6D_6$, 25° C.) δ=69.41.

Minor Isomer of Compound C3 (28%)

$^1$H-NMR (300 MHz, $C_6D_6$, 25° C.) δ=1.04 (d, $J_{HH}$=6.6 Hz, 3H, $CH_{3i-Pr}$), 1.03-1.16 (m, 9H, $CH_{3i-Pr}$), 1.19-1.29 (m, 2H, $CH_2$), 1.19-1.29 (m, 9H, $CH_{3i-Pr}$), 1.34-1.43 (m, 1H, $CH_2$), 1.34-1.44 (m, 9H, $CH_{3i-Pr}$), 1.60-1.76 (m, 3H, $CH_2$), 2.41 (b, 1H, $CH_{bridgehead}$), 2.58-2.76 (m, 4H, $CH_2$), 2.86 (b, 1H, $CH_{bridgehead}$), 3.30 (sept, $J_{HH}$=1.7 Hz, 1H, $CH_{i-Pr}$), 3.41-4.04 (m, 5H, $OCH_2$, $CH_{i-Pr}$), 7.11-7.24 (m, 3H, $CH_{Ar}$); $^{13}C\{^1H\}$-NMR (75 MHz, $C_6D_6$, 25° C.) δ=20.65 (s, $CH_{3i-Pr}$), 21.73 (d, $J_{PC}$=3.9 Hz, $CH_{3i-Pr}$), 21.80 (d, $J_{PC}$=1.9 Hz, $CH_{3i-Pr}$), 22.17 (d, $J_{PC}$=4.0 Hz, $CH_{3i-Pr}$), 24.19 (s, $CH_{3i-Pr}$), 25.34 (s, $CH_{3i-Pr}$), 25.43 (s, $CH_{3i-Pr}$), 26.29 (s, $CH_{3i-Pr}$), 26.40 (s, $CH_2$), 27.77 (s, 2C, $CH_3$, $CH_{i-Pr}$), 28.80 (s, $CH_{i-Pr}$), 30.10 (d, $J_{PC}$=1.8 Hz, $CH_2$), 40.24 (d, $J_{PC}$=1.7 Hz, $CH_2$), 41.43 (s, $CH_2$), 41.44 (d, $J_{PC}$=4.6 Hz, $CH_{bridgehead}$), 43.84 (d, $J_{PC}$=13.2 Hz, $CH_{bridgehead}$), 45.34 (d, $J_{PC}$=6.9 Hz, $CH_{i-Pr}$), 45.78 (d, $J_{PC}$=11.5 Hz, $CH_{i-Pr}$), 48.72 (d, $J_{PC}$=3.4 Hz, $CH_2$), 62.17 (d, $J_{PC}$=10.7 Hz, $CH_2$), 92.93 (d, $J_{PC}$=16.5 Hz, PC), 123.83 (s, $CH_{Ar}$), 124.27 (s, $CH_{Ar}$), 126.49 (s, $CH_{Ar}$), 140.95 (d, $J_{PC}$=2.7 Hz, $C_{Ar}$), 146.90 (s, $C_{Ar}$), 147.75 (s, $C_{Ar}$), 188.86 (d, $J_{PC}$=40.6 Hz, NC); $^{31}P\{^1H\}$-NMR (121 MHz, $C_6D_6$, 25° C.) δ=62.51.

Example 4: Study of the Catalytic Activity of Compounds C1, C2 and C3 on the Hydrosilylation Reaction of Trifluoroacetophenone with Phenylsilane Compound C1 (34 mg, 0.055 mmol), 0.4 mL of deuterated benzene ($C_6D_6$) and phenylsilane (7.5 μL, 0.06 mmol) were mixed, and 20 equivalents of trifluoroacetophenone and of phenylsilane were then respectively added. In the composition, the molar concentration of compound C1 is 5% relative to the trifluoroacetophenone. The tube was then heated to 120° C. and, after 3 hours, the $^{31}$P and $^{19}$F NMR analyses confirmed that the hydrosilylation reaction of the trifluoroacetophenone with the phenylsilane was complete, with a 100% conversion.

Compound C2 (31.6 mg, 0.055 mmol), 0.3 mL of deuterated benzene ($C_6D_6$) and phenylsilane (7.5 μL, 0.06 mmol) were mixed, and 40 equivalents of trifluoroacetophenone and of phenylsilane were then respectively added. In the composition, the molar concentration of compound C2 is 2.5% relative to the trifluoroacetophenone. The tube was then heated to 80° C. and, after 9 hours, the $^{31}$P and $^{19}$F NMR analyses confirmed that the hydrosilylation reaction of the trifluoroacetophenone with the phenylsilane was complete, with a 100% conversion.

Compound C3 (32 mg, 0.055 mmol), 0.3 mL of deuterated benzene ($C_6D_6$) and phenylsilane (7.5 μL, 0.06 mmol) were mixed, and 40 equivalents of trifluoroacetophenone and of phenylsilane were then respectively added at room temperature. In the composition, the molar concentration of compound C3 is 2.5% relative to the trifluoroacetophenone. After 3 hours at room temperature, the $^{31}$P and $^{19}$F NMR analyses confirmed that the hydrosilylation reaction of the trifluoroacetophenone with the phenylsilane was complete, with a 100% conversion.

Example 5: Study of the Catalytic Activity of Compounds C2 and C3 on the Hydrosilylation Reaction of Diethyl Ketone with Phenylsilane Compound C2 (31.6 mg, 0.055 mmol), 0.3 mL of deuterated benzene ($C_6D_6$) and phenylsilane (7.5 μL, 0.06 mmol) were mixed, and 40 equivalents of diethyl ketone and of phenylsilane were then respectively added. In the composition, the molar concentration of compound C2 is 2.5% relative to the diethyl ketone. The tube was then heated to 80° C. and, after 3 hours, the $^{31}$P and $^{19}$F NMR analyses confirmed that the hydrosilylation reaction was complete, with a 100% conversion.

Compound C3 (32 mg, 0.055 mmol), 0.3 mL of deuterated benzene ($C_6D_6$) and phenylsilane (7.5 μL, 0.06 mmol) were mixed, and 40 equivalents of diethyl ketone and of phenylsilane were then respectively added. In the composition, the molar concentration of compound C3 is 2.5% relative to the diethyl ketone. The tube was then heated to 120° C. and, after 2 hours, the $^{31}$P and $^{19}$F NMR analyses confirmed that the hydrosilylation reaction was complete, with a 100% conversion.

Example 6: Study of the Catalytic Activity of Compounds C1 and C3 on the Hydrosilylation Reaction of 4-fluorobenzaldehyde with Phenylsilane Compound C1 (34 mg, 0.055 mmol), 0.4 mL of deuterated benzene ($C_6D_6$) and phenylsilane (7.5 μL, 0.06 mmol) were mixed, and 20 equivalents of 4-fluorobenzaldehyde and of phenylsilane were then respectively added. In the composition, the molar concentration of compound C1 is 5% relative to the 4-fluorobenzaldehyde. The tube was then heated to 120° C. and, after 6 hours, the $^{31}$P and $^{19}$F NMR analyses confirmed that the hydrosilylation reaction was complete, with a 100% conversion.

Compound C3 (32 mg, 0.055 mmol), 0.3 mL of deuterated benzene ($C_6D_6$) and phenylsilane (7.5 μL, 0.06 mmol) were mixed, and 40 equivalents of 4-fluorobenzaldehyde and of phenylsilane were then respectively added. In the composition, the molar concentration of compound C3 is 2.5% relative to the 4-fluorobenzaldehyde. The tube was then heated to 80° C. After 3 days, the reaction was terminated and the $^{31}$P and $^{19}$F NMR analyses confirmed that the hydrosilylation reaction took place, with a 71% conversion.

Example 7: Study of the Catalytic Activity of Compounds C1, C2 and C3 on the Hydrosilylation Reaction of Hexanal with Phenylsilane Compound C1 (34 mg, 0.055 mmol), 0.4 mL of deuterated benzene (C$_6$D$_6$) and phenylsilane (7.5 µL, 0.06 mmol) were mixed, and 20 equivalents of hexanal and of phenylsilane were then respectively added. In the composition, the molar concentration of compound C1 is 5% relative to the hexanal. The tube was then heated to 80° C. and, after 15 hours, the $^{31}$P and $^{19}$F NMR analyses confirmed that the hydrosilylation reaction was complete, with a 100% conversion.

Compound C2 (31.6 mg, 0.055 mmol), 0.3 mL of deuterated benzene (C$_6$D$_6$) and phenylsilane (7.5 µL, 0.06 mmol) were mixed, and 40 equivalents of hexanal and of phenylsilane were then respectively added. In the composition, the molar concentration of compound C2 is 2.5% relative to the hexanal. The tube was then heated to 80° C. After 3 days, the $^{31}$P and $^{19}$F NMR analyses confirmed that the hydrosilylation reaction was complete, with a 100% conversion.

Compound C3 (32 mg, 0.055 mmol), 0.3 mL of deuterated benzene (C$_6$D$_6$) and phenylsilane (7.5 µL, 0.06 mmol) were mixed, and 40 equivalents of hexanal and of phenylsilane were then respectively added. In the composition, the molar concentration of compound C3 is 2.5% relative to the hexanal. The tube was then heated to 80° C. After 3 days, the reaction was stopped and the $^{31}$P and $^{19}$F NMR analyses confirmed that the hydrosilylation reaction took place, with a 95% conversion.

The invention claimed is:

1. An organic compound (C) represented by Formula 1:

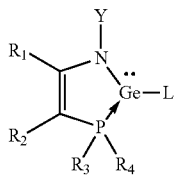

Formula 1 in which
L is an alkoxy group comprising from 1 to 18 carbon atoms,
Y is an alkyl group containing from 1 to 20 carbon atoms or an aryl group containing from 6 to 18 carbon atoms,
the groups R$_1$ and R$_2$, which may be identical or different, represent a hydrogen atom, an alkyl group containing from 1 to 20 carbon atoms, an alkenyl group containing from 2 to 12 carbon atoms, an aryl group containing from 6 to 18 carbon atoms, or R$_1$ and R$_2$ together possibly forming a saturated or unsaturated, substituted ring of 5 to 8 atoms, and in the phosphine group

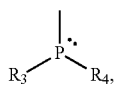

the groups R$_3$ and R$_4$, which may be identical or different, represent a hydrogen atom, a halogen atom, an alkyl or a haloalkyl group containing from 1 to 20 carbon atoms, a cycloalkyl group containing from 3 to 20 carbon atoms, a cycloalkyl-alkyl group containing from 4 to 40 carbon atoms, an aryl group containing from 6 to 18 carbon atoms, an aryl-alkyl group containing from 6 to 38 carbon atoms;

R$_3$ and R$_4$ also possibly forming, with the atoms to which they are attached, a monocyclic or polycyclic ring consisting of 3 to 20 atoms.

2. The compound as claimed in claim 1, wherein the phosphine group is represented by the formulae:

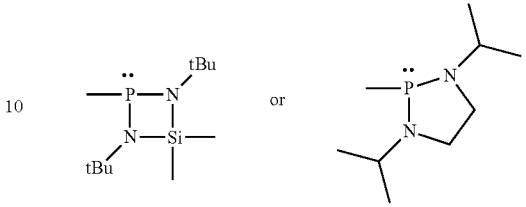

in which tBu is the tert-butyl group.

3. The compound as claimed in claim 1, wherein L is an alkoxy group chosen from methoxy, ethoxy, propoxy and butoxy.

4. The compound as claimed in claim 1 wherein L is an ethoxy group.

5. The compound as claimed in claim 1, wherein R$_1$ and R$_2$ together form a saturated or unsaturated substituted ring of 5 to 8 atoms, in which two of the substituents form a bridge of 1 to 3 atoms on said ring.

6. The compound as claimed in claim 1, wherein the organic compound (C) of Formula 1 has the following structure:

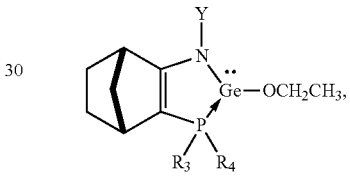

wherein
Y is 2,6-iPr$_2$—C$_6$H$_3$, and
the phosphine group is represented by the formulae:

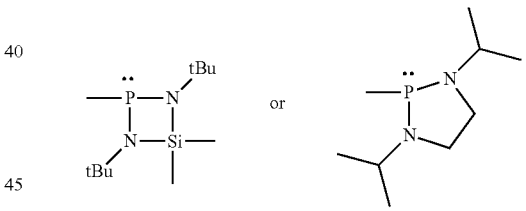

in which tBu is the tert-butyl group.

7. The compound as claimed in claim 1, wherein the organic compound (C) has the following structure:

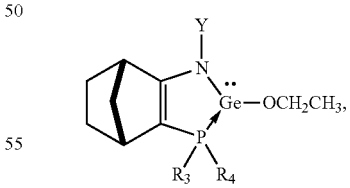

in which
Y is 2,4,6-trimethyl-C$_6$H$_2$, and
the phosphine group is represented by the formula:

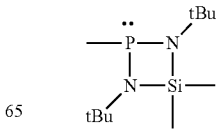

in which tBu is the tert-butyl group.

8. A product comprising an organic compound (C) as claimed in claim 1, as a hydrosilylation catalyst.

9. A composition comprising:
at least one unsaturated compound (A) comprising at least one ketone function, aldehyde function, alkene function and/or alkyne function,
at least one compound (B) comprising at least one hydrogenosilyl function, and
a catalyst chosen from the organic compounds (C) as claimed in claim 1.

10. The composition as claimed in claim 9, wherein the molar concentration of catalyst in the composition is from 0.5% to 10%, relative to the number of moles of unsaturated compound (A).

11. The composition as claimed in claim 9, wherein the molar concentration of catalyst in the composition is from 1.5% to 5.5% relative to the number of moles of unsaturated compound (A).

12. The compound as claimed in claim 1, wherein L is a linear alkoxy group with 1 to 18 carbon atoms.

13. A process for the hydrosilylation of an unsaturated compound (A) comprising at least one ketone function, aldehyde function, alkene function and/or alkyne function, with a compound (B) comprising at least one hydrogenosilyl function, wherein said process comprises catalysing with the organic compound (C) according to claim 1.

14. The process as claimed in claim 13, wherein the unsaturated compound (A) comprises one or more alkene or alkyne functions and from 2 to 40 carbon atoms.

15. The process as claimed in claim 13, wherein compound (B) comprises at least one hydrogenosilyl function chosen from:

a silane or polysilane compound comprising at least one hydrogen atom bonded to a silicon atom,
an organopolysiloxane compound comprising at least one hydrogen atom bonded to a silicon atom, and an organic polymer comprising hydrogenosilyl functions in end positions.

16. The process as claimed in claim 13, wherein:
the unsaturated compound (A) is chosen from organopolysiloxane compounds comprising units of formula (I):

$$A_g U_b SiO_{(4-(g+h))/2} \quad (I)$$

in which:
the radicals A, which may be identical or different, represent a linear or branched alkenyl or alkynyl radical containing between 2 and 6 carbon atoms;
the radicals U, which may be identical or different, represent a monovalent radical other than a hydrogen atom,
g and h represent integers, g being 1 or 2, h being 0, 1 or 2 and (g+h) being 1, 2 or 3;
compound (B) comprising at least one hydrogenosilyl function is an organopolysiloxane comprising at least one unit of formula (III):

$$H_d U_e SiO_{(4-(d+e))/2} \quad (III)$$

in which:
U has the same meaning as above,
d and e represent integers, d being 1 or 2, e being 0, 1 or 2 and (d+e) being 1, 2 or 3.

* * * * *